(12) United States Patent
Goetz

(10) Patent No.: US 12,035,899 B2
(45) Date of Patent: Jul. 16, 2024

(54) MEDICAL APPARATUS AND METHOD FOR CLOSING AN OPENING IN A TISSUE

(71) Applicant: Venock Medical GmbH, Regensburg (DE)

(72) Inventor: Wolfgang Goetz, Regensburg (DE)

(73) Assignee: VENOCK MEDICAL GMBH, Regensburg (DE)

(*) Notice: Subject to any disclaimer, the term of this patent is extended or adjusted under 35 U.S.C. 154(b) by 675 days.

(21) Appl. No.: 16/970,462

(22) PCT Filed: Feb. 28, 2019

(86) PCT No.: PCT/EP2019/055035
§ 371 (c)(1),
(2) Date: Aug. 17, 2020

(87) PCT Pub. No.: WO2019/166573
PCT Pub. Date: Sep. 6, 2019

(65) Prior Publication Data
US 2020/0375584 A1    Dec. 3, 2020

(30) Foreign Application Priority Data

Feb. 28, 2018 (DE) .......................... 102018104549.2

(51) Int. Cl.
 *A61B 17/00*   (2006.01)
 *A61B 17/064*  (2006.01)
 *A61B 17/10*   (2006.01)

(52) U.S. Cl.
 CPC ...... *A61B 17/0057* (2013.01); *A61B 17/0644* (2013.01); *A61B 17/10* (2013.01);
 (Continued)

(58) Field of Classification Search
None
See application file for complete search history.

(56) References Cited

U.S. PATENT DOCUMENTS 4,217,902 A    8/1980  March
5,674,231 A    10/1997 Green et al.
(Continued)

FOREIGN PATENT DOCUMENTS

AU    2010227037 B2    4/2015
CA       2188210 C     3/2006
(Continued)

OTHER PUBLICATIONS

International Search Report and Written Opinion for PCT/EP2019/055035 mailed Jun. 5, 2019.

*Primary Examiner* — Shaun L David
(74) *Attorney, Agent, or Firm* — Aird & McBurney LP

(57) ABSTRACT

The present invention relates to a medical apparatus for closing an aperture, an incision, a puncture, a passage through tissue and/or a communication with a blood vessel or other body lumen (short: aperture) of a tissue of a patient, the medical apparatus comprising a closing device holder, for releasably receiving one or more closing devices; and a retracting unit to come into contact with opposite sides of the aperture and for retracting them and/or for spreading the aperture causing it to change its shape into a slit or a slit-like or a more slit-like aperture or to spread or to augment the dimension or diameter of the aperture in at least one or in exactly one dimension of the aperture.

29 Claims, 37 Drawing Sheets

(52) U.S. Cl.
CPC ............... *A61B 2017/00004* (2013.01); *A61B 2017/00623* (2013.01); *A61B 2017/00663* (2013.01); *A61B 2017/00668* (2013.01); *A61B 2017/00867* (2013.01)

(56) References Cited

U.S. PATENT DOCUMENTS

| | | | |
|---|---|---|---|
| 5,766,189 | A | 6/1998 | Matsuno |
| 5,964,782 | A | 10/1999 | Lafontaine et al. |
| 6,358,258 | B1 | 3/2002 | Arcia et al. |
| 6,391,048 | B1 | 5/2002 | Ginn et al. |
| 6,533,762 | B2 | 3/2003 | Kanner et al. |
| 6,726,704 | B1 | 4/2004 | Loshakove et al. |
| 6,767,356 | B2 | 7/2004 | Kanner et al. |
| 7,628,306 | B2 | 12/2009 | Spurchise et al. |
| 7,740,640 | B2 | 6/2010 | Ginn |
| 7,744,610 | B2 | 6/2010 | Hausen |
| 7,875,053 | B2 | 1/2011 | Bender et al. |
| 7,942,301 | B2 | 5/2011 | Sater |
| 8,282,654 | B2 | 10/2012 | Ferrari et al. |
| 8,317,807 | B1 | 11/2012 | Post |
| 8,545,974 | B2 | 10/2013 | Creasy, Jr. |
| 8,758,398 | B2 | 6/2014 | Carley |
| 8,932,324 | B2 | 1/2015 | Sibbit, Jr. et al. |
| 9,585,647 | B2 | 3/2017 | Clark |
| 9,668,724 | B2 | 6/2017 | Tang et al. |
| 9,980,728 | B2 | 5/2018 | Cummins et al. |
| 10,111,664 | B2 | 10/2018 | Ginn et al. |
| 10,143,460 | B2 | 12/2018 | Green |
| 2001/0053922 | A1 | 12/2001 | Zhu et al. |
| 2002/0107542 | A1 | 8/2002 | Kanner et al. |
| 2002/0133193 | A1 | 9/2002 | Ginn et al. |
| 2003/0045893 | A1 | 3/2003 | Ginn |
| 2005/0059985 | A1 | 3/2005 | Kimura |
| 2006/0282118 | A1 | 12/2006 | Surti |
| 2007/0049967 | A1 | 3/2007 | Sibbitt, Jr. et al. |
| 2007/0049968 | A1 | 3/2007 | Sibbitt et al. |
| 2008/0221599 | A1* | 9/2008 | Starksen ............... A61B 17/068 606/157 |
| 2008/0221614 | A1 | 9/2008 | Mas |
| 2008/0300628 | A1 | 12/2008 | Ellingwood |
| 2008/0312666 | A1 | 12/2008 | Ellingwood et al. |
| 2008/0319455 | A1* | 12/2008 | Harris ............... A61B 17/0684 606/139 |
| 2009/0039138 | A1 | 2/2009 | Bender et al. |
| 2009/0259249 | A1 | 10/2009 | Lobello |
| 2010/0160958 | A1 | 6/2010 | Clark |
| 2010/0228286 | A1 | 9/2010 | Ginn |
| 2011/0054521 | A1 | 3/2011 | Ventura et al. |
| 2012/0209318 | A1 | 8/2012 | Qadeer |
| 2015/0039008 | A1 | 2/2015 | Suzuki et al. |
| 2015/0066055 | A1 | 3/2015 | Sibbitt, Jr. et al. |
| 2017/0049426 | A1 | 2/2017 | Gianotti et al. |
| 2018/0193600 | A1 | 7/2018 | Kassab et al. |
| 2018/0256139 | A1 | 9/2018 | Miller et al. |
| 2018/0256166 | A1 | 9/2018 | Cummins et al. |
| 2020/0345367 | A1* | 11/2020 | Greenberg ............... A61B 17/08 |

FOREIGN PATENT DOCUMENTS

| | | |
|---|---|---|
| CN | 201668444 U | 12/2010 |
| DE | 299 23 269 U1 | 8/2000 |
| JP | 2003518975 A | 6/2003 |
| JP | 2008505697 A | 2/2008 |
| WO | 2001049186 A2 | 7/2001 |
| WO | 2006017023 A2 | 2/2006 |
| WO | 2007025018 A2 | 3/2007 |
| WO | 2007025019 A2 | 3/2007 |
| WO | 2008150915 A1 | 12/2008 |
| WO | 2010081103 A1 | 7/2010 |
| WO | 2019135236 A1 | 7/2019 |
| WO | 2019166573 A1 | 9/2019 |

* cited by examiner

MEDICAL APPARATUS AND METHOD FOR CLOSING AN OPENING IN A TISSUE

The present invention relates to a medical apparatus for closing an aperture according to the preamble of claim 1 and a method for closing an aperture according to the preamble of claim 27.

The present invention relates generally to a medical apparatus (in short: apparatus) and methods for engaging tissue and/or closing openings through tissue, and more particular for closing apertures in a blood vessel or other body lumen, which is an alternative to suturing; and, more particularly, relates to a closure apparatus having applications for closure of openings in body organs or blood vessel walls, in particular after invasive procedures in a patient's system, and corresponding methods of use.

There exist several interventional procedures which are generally performed by puncture and inserting a hollow needle in a blood vessel or other body organ, a guide wire may then be advanced through the needle lumen into the patient's blood vessel or other organs. The guide-wire may be advanced through the needle and the needle may be removed and an introducer casing may be advanced over the guide wire into the vessel or other body organ (Seldinger technique). Such casings are generally flexible tubes having thin walls and diameters matching the needs of the utilized treatment system in the range of up to about 30 F or more. The proximal end of the casing is retained outside of the skin of the patient, commonly utilized with a hemostatic valve to prevent blood flow from the blood vessel through the casing. A catheter or other device may then be advanced through a lumen of the introducer casing and over the guide-wire into a position for performing a medical procedure. The punctures are utilized for a number of reasons including, but not limited to, diagnostic cardio-vascular procedures, coronary and peripheral angioplasties or stenting, heart valve prosthesis implantation and heart valve repair, thoracoscopic, laparoscopic or endoscopic surgery, and the like. These procedures all require making a puncture in body organs or in the wall of a blood vessel to be used in the treatment of the patient's system. The size of the puncture will vary depending on the procedure and the inserted system. Depending on the procedure, commonly the femoral artery or the femoral vein is utilized as point of entry into the patient's system. Typical punctures can range from 2 mm to more than 10 mm in diameter, or from 6 F to more than 30 F for interventional procedures.

Other procedures, such as may be encountered with the use of endoscopes or other instruments, may utilize trocars for insertion. Typical trocar punctures can range from 2 mm to more than 15 mm in diameter, or from 6 F to more than 45 F. Closure of such openings is typically accomplished using multiple levels of surgical sutures.

Upon completing the interventional diagnostic or treatment procedures utilizing vascular puncture as access site, whether of the peripheral circulation, the coronary circulation system or the heart, the devices and introducer casing may be removed, leaving a puncture site in the vessel wall or in the body organ.

Such perforations can be closed and sutured tight with common open surgical methods utilizing a single knot or running surgical sutures.

An alternative open procedure to stop the bleeding is the use of clips or staples. One form of a hemostatic clip is shown in U.S. Pat. No. 4,217,902 by March et al. that requires open surgical access of the perforation to allow operation of the clamping mechanism. And more sophisticated surgical staplers are described, as shown in US 2008/0272173 by Coleman James et al., that require an open access.

Various procedures and devices have been developed to address the hemostasis after perforation of a blood vessel for a diagnostic or treatment procedure in a closed, non-surgical way.

A common way to stop the bleeding is by applying pressure to the location of the perforation and waiting for the natural blood clotting and self-healing characteristics of the patient to seal the vessel opening. Such pressure may be required for relatively long time, such as 30 minutes to up to an hour, followed by the patient being bedridden during this time, essentially immobilized and with a heavy sandbag placed on the punctuation site to provide compression for several hours until the bleeding has stopped. Additional risk of hematoma exists from bleeding before complete hemostasis and sealing occur. This procedure may be time consuming with related downsides.

With the increasing size of the vessel perforation like in heart valve prosthesis implantation or heart valve repair systems, the compression of the perforation and waiting for the natural sealing of the opening becomes less effective or even ineffective.

While excessive bleeding can occur already in persons having a normal blood clotting response, there are patients who are utilizing anticoagulation medications which inhibit clotting, suffer from bleeding disorders, hypertension or obesity, which increases the risk of excessive bleeding following removal of the penetrating casing or treatment systems.

An improved way to stop the bleeding is by applying a collagen or polymer plug as shown in U.S. Pat. No. 5,275, 616. Such procedure is effective especially in smaller perforations. However, placement of such plug material adds to the risk of intravascular thrombus formation and development of an inflammatory reaction.

Various percutaneous clips or staplers were developed to avoid an open access closure. The systems are inserted over the already utilized guide wire and the clips are operated percutaneously.

Various percutaneous suturing systems have been developed having closure systems that provide a plurality of needles that are joined by a suture. After the needles have passed through the vascular wall surrounding an opening, they are captured, drawn outward, tied and the knot pushed back through the tract to complete the closure. The placement of the suture needles requires an adequate engagement of tissue such that the placed sutures can hold and close the hole, which limits the system to the closure of rather smaller vascular perforations.

In procedures with perforations of body cavities and organs like thoracoscopic, laparoscopic or endoscopic surgeries, it is common to make an entry to the patient's body with a trocar of suitable size, large enough to insert the applicable system. Closure of such large bore perforations is commonly done by open surgical suturing.

An object of the present invention may be to propose a further medical apparatus for closing an aperture and a method thereto.

The above-mentioned object is achieved by the medical apparatus for closing an aperture having the features of claim 1. It is further achieved by the method for closing an aperture having the features of claim 27.

In all of the aforementioned and following statements, the use of the expressions "may be" or "may have" and so on, is to be understood synonymously with "preferably is" or "preferably has", and so on respectively, and is intended to illustrate an embodiment according to the present invention.

Whenever numerical words are mentioned herein, the person skilled in the art shall recognize or understand them as indications of numerical lower limits. Hence, unless this leads to a contradiction evident for the person skilled in the art, the person skilled in the art shall comprehend for example "one" as encompassing "at least one". This understanding is also equally encompassed by the present invention as the interpretation that a numerical word, for example, "one" may alternatively mean "exactly one", wherever this is evidently technically possible in the view of the person skilled in the art.

Both of these understandings are encompassed by the present invention and apply herein to all used numerical words.

The present invention thus proposes a medical apparatus for closing an aperture, an incision, a puncture, a passage through tissue and/or a communication with a blood vessel or other body lumen (in short: aperture) of a tissue of a patient. Herein, the medical apparatus comprises a closing device holder for releasably receiving and/or holding one or more closing devices. The medical apparatus further comprises a retracting unit which comes into contact with opposite sides of the aperture in order to retract them and/or in order to spread the aperture, optionally causing it to change its shape into a slit or a slit-like or a more slit-like aperture. This change may result in spreading or augmenting the dimension or diameter of the aperture in at least one or in exactly one dimension of the aperture.

Moreover, a method for closing an aperture of a tissue is proposed. The method encompasses firstly the step of providing a medical apparatus according to the present invention and secondly the step of closing the aperture by using the medical apparatus.

Advantageous developments of the present invention are each subject-matter of the dependent claims and embodiments.

Whenever an embodiment is mentioned herein, it represents an exemplary embodiment according to the present invention.

Embodiments according to the present invention may comprise one or several of the features mentioned supra and/or in the following in any combination which is technically possible.

In some embodiments, the retracting unit of the medical apparatus according to the present invention comprises at least one retracting device holder and at least one retracting device. The latter may preferably be at least partially received in the retracting device holder. The retracting device may optionally be at least partially received in the retracting device holder, preferably in a releasable manner, and is preferably arranged there in a moveable or slidable manner with respect to the retracting device holder.

The retracting device holder may have both a distal end, preferably configured to be advanced or extended through or into the aperture to be closed, and a proximal end.

In several embodiments, the retracting unit of the medical apparatus according to the present invention comprises at least one engaging device connected to said retracting device in order to releasably engage with the tissue.

In some embodiments, the engaging device may have a closed section having a through-opening. The closed section may have the shape of a rectangle, a square, a circle, an ellipse, or combinations thereof.

In several embodiments, the engaging device may comprise a wire or consist of a wire.

In some embodiments, the engaging device may be formed from a single wire.

In several embodiments, the engaging device may have or cover a convex or concave shape. In other embodiments it is flat or substantially plane.

In some embodiments, the engaging device of the medical apparatus according to the present invention is configured to be foldable and/or to be comprised or captured at least partially within the retracting device holder.

A mechanism for moving the engaging device and/or the retracting device into or out of the retracting device holder may be provided.

In several embodiments, the engaging device may be connected to the above-mentioned retracting device such that they are configured for engaging with the tissue surrounding the aperture from within or from below the aperture opening.

In some embodiments, at least two retracting devices and/or at least two engaging devices of the medical apparatus according to the present invention are captured within the retracting device holder in a releasable manner. In particular, they are captured such that they are arranged to be at least partly released from the retracting device holder by manipulating the retracting device holder or the engaging device or a mechanism configured to do so when required, in particular in order to be positioned below the opening level of the aperture to be closed.

In several embodiments, the retracting device holder and/or the retracting device and/or said engaging device of the medical apparatus according to the present invention are configured to retract the opposite sides of the aperture, in particular such that the aperture changes its shape. For example, the aperture may change from a rather round shape to a slit aperture. Preferably, this results in an extended transverse diameter that is at least double the length of the retracted longitudinal diameter of the aperture. "Transverse" may refer to a direction perpendicular to the longitudinal direction of the vessel. The longitudinal diameter may run in the direction of the longitudinal axis of the vessel.

In some embodiments, the retracting unit of the medical apparatus according to the present invention comprises at least a retracting device having at least one of the following:
  a first side and an opposite second side,
  a first arm and a second arm,
  a first retracting device and a second retracting device,
  a first retracting device holder and a second retracting device holder, and/or
  a first engaging device and a second engaging device.

Additionally, the retracting unit or any other component may have a mechanism for moving the first side apart or away from the second side, the first arm apart or away from the second arm, the first retracting device apart or away from the second retracting device, the first retracting device holder apart or away from the second retracting device holder and/or the first engaging device apart or away from the second engaging device.

In several embodiments, the above-mentioned mechanism comprises or consists of a shape memory characteristic.

In some embodiments, the mechanism may comprise or consist of a mechanical means comprising, e. g., gears, rods, an actuating means, a control means such as a knob or handle, and the like.

In several embodiments, the mechanism may comprise or consist of a vacuum device configured to amend the shape of the retracting device, the retracting unit or any other component such that the first side or the first arm, and so on, is moved apart or away from the second side or the second arm, and so on.

The vacuum device may be arranged to suck a fluid (e. g., air) from an inner, preferably closed, lumen of, e.g., the retracting unit such that the cross section of that component, e.g. the retracting unit, is changed: by attempting to achieve a vacuum inside the lumen, the cross section of, e.g., the retracting unit will increase in a first dimension but decrease in a second dimension perpendicular to the first one. That way, opposite first and second sides of, e.g., the retracting unit will move away from each other while the circumference of the retracting unit is kept constant.

The preferably closed lumen which is in fluid communication with the vacuum device may in at least one state (having applied vacuum or not) have a cross section that is longer in a first direction thereof than in a second direction perpendicular to the first one.

In some embodiments, the retracting unit or the retracting device has a curve or a step or it bends on its front side or on its rear side that might be used as a stop or give the surgeon tactile feedback while partly withdrawing the medical apparatus from the vessel lumen. The curve, step or the like may indicate that the tip of the medical apparatus, or its retracting unit, retracting device or the like has come to rest at the rim of the vessel or the aperture. This, in turn, indicates that the medical apparatus is in a suitable position for deploying the closing device. To achieve this, the curve, step or the like is arranged under a pre-determined distance from, e. g., the free end of the medical apparatus or the retracting device. Also, the curve, step or position at which it is bent may serve as protection against pulling the medical apparatus too far out from the vessel lumen before releasing the closing device.

In several embodiments, the medical apparatus according to the present invention comprises a closing device comprised in the closing device holder.

In some embodiments, the closing device of the medical apparatus according to the present invention is at least partially comprised within the closing device holder in a stressed state of the closing device. In particular, it is comprised within the distal end of the closing device holder, in particular when the closing device is in an undeployed state. Herein, the closing device has preferably two or more ends and a junction connecting with the two or more ends, e. g., via two or more arms.

In several embodiments, the closing device of the medical apparatus according to the present invention is comprised within the closing device holder such that when the closing device is manipulated to exit the distal end of the closing device holder during the use of the medical apparatus, the closing device releases its stress, or part of it, e.g., by bending the two or more arms outside of the closing device holder. Thereby, the two or more ends are arranged to perforate the inner wall of the tissue surrounding the aperture.

In some embodiments, at least part of the closing device, the retracting device, the retracting device holder and/or the engaging device of the medical apparatus according to the present invention is made of a deformable shape memory alloy and/or has a self-expanding shape memory section or a wire body.

In several embodiments, at least part of the closing device, the retracting device, the retracting device holder and/or the engaging device of the medical apparatus according to the present invention is made of Nitinol.

In some embodiments, at least part of the closing device, the retracting device, the retracting device holder and/or the engaging device of the medical apparatus according to the present invention is made of biocompatible and/or bioabsorbable material.

In several embodiments, the biocompatible and/or bioabsorbable material is at least one material selected from the group consisting of Ti, Ti alloys, Nitinol, stainless steel, polymeric materials, and ceramic.

In some embodiments of the medical apparatus according to the present invention, the closing device or parts thereof curl into a closed form (having, e.g., a through-opening surrounded by arm, struts or the like of the closing device) when in a stress-free state.

In several embodiments of the medical apparatus according to the present invention, the closing device or parts thereof curl into a loop- or ring- or circle-like shape when in a stress-free state.

In several embodiments of the medical apparatus according to the present invention, the closing device after deployment has a cross-sectional dimension ranging from 10 micrometers to 1 centimeter, preferably from 40 micrometers to 200 micrometers, more preferably from 50 micrometers to 100 micrometers.

In some embodiments, the medical apparatus according to the present invention further comprises a pushing device, preferably extending through the proximal end of the closing device holder, for the manipulation of the closing device. The pushing device may be configured not to deform the closing device by acting on it, e.g., by pushing it.

In several embodiments of the medical apparatus according to the present invention, the pushing device is or comprises a rod or a piston.

In some embodiments, the medical apparatus according to the present invention further comprises a holding or withdrawing device extending through the proximal end of the closing device holder for the manipulation of the closing device. Herein, said holding device is, in particular releasably, attached to the closing device or connected therewith.

In several embodiments, the holding device of the medical apparatus according to the present invention is a string or a suture.

In some embodiments, the closing device holder of the medical apparatus according to the present invention has one or more grooves on the inner wall of the closing device holder and/or one or more grooves on the pushing device for guiding the holding device along the longitudinal direction of the closing device holder, preferably through or along the groove(s).

In several embodiments of the medical apparatus according to the present invention, the distal end of the closing device holder has two or more channels on the wall of the closing device holder. These channels allow one or more ends of the closing device to exit the closing device holder upon manipulation of the medical apparatus or when required by the user. The ends may exit from one side or both sides of the closing device holder. The channels may be slit-like. The channels or the proximal ends thereof may be exceeded in a distal direction of the closing device holder by the distal end.

In some embodiments of the medical apparatus according to the present invention, the distal end of the closing device holder has at least one channel or two channels arranged opposite to each other on the wall, in particular in the circumference of the closing device holder, of the closing device holder.

In several embodiments of the medical apparatus according to the present invention, the retracting device holder is or comprises an elongated tube. This elongated tube comprises or consists of, e.g., metal or plastic and is preferably configured to capture a retracting device. The closing device holder may have a distal end for being advanced or extended through or into the aperture of the tissue, and a proximal end in particular suitable for providing access for manipulating a closing device when and if received in the closing device holder.

In some embodiments, at least one of the closing device holder and the retracting unit is at least one of slidably and moveably arranged within the medical apparatus with respect to each other, to other elements of the medical apparatus, and/or to a casing or an outer sheath of the medical apparatus.

In some embodiments, the medical apparatus comprises an outer housing, sheath or casing that comprises some or all elements (except for the housing or casing and the like, of course) of the medical apparatus, in particular the closing device holder and/or the retracting unit.

In some embodiments, the medical apparatus comprises a lumen for guiding and/or encompassing a guide wire. The lumen may be open to both the distal end and the proximal end of the medical apparatus or to just one of those.

In some embodiments, the medical apparatus comprises several lumen or openings. One of them may house a first closing device holder, another one may house a second closing device holder, a retracting device holder and/or any other element of the medical apparatus, for example.

Any lumen of the medical apparatus may be a through-opening of the medical apparatus, preferably extending in a longitudinal direction of the medical apparatus.

In some embodiments the medical apparatus has an outer housing or unit that is, along its entire length or along only parts of it, not flexible and/or flexible.

In several embodiments of the method according to the present invention, the method comprises the following further steps:
  introducing parts of the retracting unit into the aperture;
  contacting opposite sides of the aperture with the retracting unit or elements comprised by it;
  retracting the opposite sides of the aperture and/or spreading the aperture with the retracting unit or elements comprised by it; and
  releasing at least one closing device from the closing device holder and connecting the opposite sides of the aperture to each other with the closing device.

In some embodiments of the method according to the present invention, the step of retracting opposite sides of the aperture and/or spreading the aperture causes the aperture to change its shape, e.g., into a slit or a slit-like or a more slit-like aperture. This change may result in spreading or augmenting the dimension or diameter of the aperture in at least one or in exactly one dimension of the aperture.

In some embodiments at least one of the closing device holder and the retracting device holder is a partly hollow tube.

In some embodiments at least one of the closing device holder and the retracting device holder are arranged within a common casing or housing, preferably slidable or moveable with respect to that casing.

In some embodiments the closing member is identical to the closing device holder.

In some embodiments the retracting unit is identical to the retracting device holder.

In some embodiments the retracting unit and the closing member are embodied by one device only.

In some embodiments the device has no guide wire. It may, however, have a lumen for running a guide wire through the length of the device and/or in the direction of its length.

In some embodiments the closing device is a staple or a clip.

In some embodiments the closing device holder is not configured to eject or to release the closing devices, in particular staples or clips, in a first direction wherein a component of the device or of the closing device holder configured to eject the closing device or to assist in ejecting them, is arranged to be moveable at best (or ideally only) in the first direction or at best substantially in the first direction. However, in those embodiments, that component is not configured or arranged to be moveable in a second direction which is substantially perpendicular to the first direction.

In some embodiments at least one of the closing device holder and the device has no devices configured for plastically deforming the closing devices, in particular not for plastically deforming them while there are rejected or released. Also, there is preferably no devices provided for closing a closing device.

In some embodiments the closing device holder is configured to simultaneously eject or release two or more closing device. For example, the closing device may be ejected from one common opening of the holder through which they leave side by side. Alternatively, the configuration may be such that two or more closing device may leave the closing device holder or the device through separate openings but at the same time.

In some embodiments, the closing device holder is configured such that the closing device can only be ejected or released in the longitudinal direction of the closing device holder.

In some embodiments, the closing device holder is configured such that the closing device can only be ejected or released at the same position with respect to the length or the longitudinal direction of the closing device holder.

In some embodiments the retracting unit comprises at least two elements that move apart from each other while retracting the aperture, for example, two sides, two arms, two retracting devices or two retracting device holders.

In some embodiments the retracting unit and the closing device holder are separate from each other, and, in particular, may move separately from each other. In other embodiments, they are interconnected to each other or embodied by the same unit such that they cannot move independently from each other.

In some embodiments the retracting unit and the closing device holder are spaced apart from each other such that the closing device holder is configured to eject or release the closing device or devices into the tissue in order to have them close the rim or seam of the long sides of aperture in retracted state of the aperture, that is while the aperture is being retracted or spread by the retracting unit.

In some embodiments at least one of the components of the retracting unit configured to retract the opposite sides of the aperture by directly touching them is an elongated or oblong section. At least one of them may have the shape of a pole, a tube or the like, and they are, preferably, straight.

In some embodiments at least one of the components of the retracting unit configured to retract opposite sides of the aperture by directly touching them (such as the first and the second arms or sections, the first and the second retracting devices, the first and the second retracing device holder and/or the first and the second engaging device) does not comprise one or more hinges, articulations, joints or sections where it bends, in particular not in a middle section thereof, more particular not facing to opposite directions from each other.

In some embodiments the components of the retracting unit configured to retract the opposite sides of the aperture by directly touching them have a free distal end.

In some embodiments, some or all of the components of the retracting unit configured to retract opposite sides of the aperture by directly touching them are configured to move with respect to each other in a first common plane while retracting the aperture. Optionally, in these or in different embodiments the at least one closing device extends (e. g., in a deployed state of the closing device, e. g., when being released or ejected) entirely or substantially in a second plane. Also, the closing device may optionally close in the second plane. For example, the closing device may comprise arms or tines that move towards each other upon closing or deploying. That movement can also take place in substantially one plane, namely the second plane. The first plane and the second plane may intersect each other. They may be substantially perpendicular to each other.

In some embodiments, some or all of the components of the retracting unit configured to retract opposite sides of the aperture by directly touching them are configured to move with respect to each other in a first direction while retracting the aperture. Optionally, in these or in different embodiments the device is configured to eject or to release the at least one closing device in a second direction. The first direction and the second direction may be different from each other. In fact, they may be perpendicular or substantially perpendicular to each other. Hence, the direction of retracting may be perpendicular or substantially perpendicular to the direction in which the closing device is ejected or released and/or in which the closing device closes when the device is used by the surgeon.

In some embodiments the first and the second retracting devices, or first and second arms or sections thereof, are connected to each other by just one hinge or joint or hinge or joint section. That hinge or joint or section may be arranged to move—preferably exclusively—inside the retracting device holder and/or along the longitudinal axis of the medical device or the of the retracting device holder. Additionally, or alternatively, that hinge or joint or section may be arranged to move—preferably exclusively—in the second direction, not, however, in the first direction. Hence, in those embodiments the hinge or joint or section may optionally not move in the direction in which the opposite sides of the aperture are retracted or spread.

According to the present invention, a medical apparatus for closing an aperture of a tissue is also suggested, comprising a closing device holder, wherein said closing device holder has a distal end for extending through the aperture of the tissue in a deployed state of the medical apparatus, and a proximal end for providing access for manipulation of a closing device; and a closing device at least partially captured in a stressed state within the distal end of the closing device holder when the medical apparatus or the closing device is in an undeployed state; wherein the closing device has two or more ends and a junction connecting with the two or more ends via two or more arms;

wherein the closing device is configured relative to the closing device holder so that when the closing device is manipulated to exit the distal end of the closing device holder during the deployment of the medical apparatus or the closing device, the closing device releases its stress by bending the two or more arms outside of the closing device holder, whereby the two or more ends perforate the inner wall of the tissue surrounding the aperture.

According to the present invention, a method for closing an aperture of a tissue is also suggested, the method encompassing the steps:

providing a medical apparatus according to the present invention;

closing the aperture by means of the medical apparatus.

In some embodiments according to the present invention, at least part of the closing device is made of a deformable shape memory alloy.

In some embodiments according to the present invention, at least part of the closing device is made of Nitinol.

In some embodiments according to the present invention, at least part of the closing device is made of biocompatible and/or bio-absorbable material.

In some embodiments according to the present invention, the biocompatible and/or bio-absorbable material is at least one material selected from the group consisting of Ti, Ti alloys, Nitinol, stainless steel, polymeric materials, and ceramic.

In some embodiments according to the present invention, the closing device curls into a closed form when in a stress-free state.

In some embodiments according to the present invention, the closing device curls into a loop- or ring- or circle-like shape when in a stress-free state.

In some embodiments according to the present invention, the closing device after deployment of the medical apparatus has a cross-sectional dimension ranging from 10 micrometers to 1 centimeter, preferable from 40 micrometers to 200 micrometers, more preferably from 50 micrometers to 100 micrometers.

In some embodiments according to the present invention, the medical apparatus comprises a pushing device extending through the proximal end of the closing device holder for the manipulation of the closing device.

In some embodiments according to the present invention, the pushing device is a rod or piston.

In some embodiments according to the present invention, the medical apparatus comprises a holding device extending through the proximal end of the closing device holder for the manipulation of the closing device, wherein said holding device is attached with the closing device.

In some embodiments according to the present invention, the holding device is a string or suture.

In some embodiments according to the present invention, the closing device holder has one or more grooves on the inner wall of the closing device holder and/or one or more grooves on the pushing device for guiding the holding device along the longitudinal direction of the closing device holder.

In some embodiments according to the present invention, the distal end of the closing device holder has two or more channels on the wall of the closing device holder, allowing the one or more ends of the closing device to exit the closing device holder when deploying the closing device.

In some embodiments according to the present invention, the distal end of the closing device holder has two channels arranged opposite to each other on the wall of the closing device holder.

Most of the systems that are state of the art like utilizing plugs, clips or sutures can only close rather smaller size arterial perforation up to 10 F and are only approved for arterial access sites. Some of the systems are used off-label for closing larger arterial or venous punctures.

The present invention may advantageously provide a more effective method and a medical apparatus for sealing large bore punctures up to 30 F and larger in veins and other passages through tissues.

The present invention allows to connect tissue segments together or to close and/or seal opening through tissue, such as very large bore vascular perforations in the venous system in particular the Vena femoralis.

Such large vascular access and perforations are required for more complex interventional procedures like transseptal mitral and tricuspid valve repair and prosthesis implantation.

The femoral vein has a diameter of approximately 8 mm or 24 F, and more, allowing introduction of systems with a similar diameter. It is very challenging to close such large bore perforations of the vein with a percutaneous system utilizing plugs, sutures or clips. When closing such large bore perforations in a circular or longitude way, the risk of a vascular stenosis is high.

According to the present invention, a particular technique is advantageously used to stretch the perforation in a direction orthogonal to the vessel long axis and to suture the perforation close along this stretch. In this way narrowing of the vessel lumen is avoided.

The present invention allows closing a large bore vascular perforation in particular in veins by stretching the perforation in an orthogonal direction to the vessel long axis and placing single clips along the stretch that close the perforation along the stretched line.

In some embodiments, the medical apparatus may include a handle member and a tube set coupled to the handle member on one side (not shown) and on the other side, retracting units and closing members that are deployed subsequently or simultaneously in a tissue aperture. The handle member may also include any number of mechanisms (not shown) necessary to deploy a retractor and closure members. The retracting units and closing members are deployed through a casing that allows these units and members to be disposed at least partially in the aperture or lumen of a vessel in a controlled manner, in particular along a guiding structure, like a guide-wire or other rail (not shown) that is commonly placed in a vessel for performing interventional procedures.

The retracting units optionally include two retracting device holders with distal ends configured for extending through the aperture and to be positioned at the opposing inner side of the aperture to be closed. The retracting devices or their holders may have engaging devices mounted at, e.g., the distal end thereof. The engaging devices may be arranged for engaging the opposing end of the aperture and of the inner vessel wall, e. g. by contacting, pushing and/or abutting them. The engaging devices are configured to move apart, retracting the opposing sides of the aperture and stretching the aperture which approximates the opposing sides of the aperture between the retracting devices, such that the aperture becomes straight with one extended long diameter and an orthogonal retracted short diameter.

The closing member optionally includes one or more closing device holders with a distal end extending through the aperture to be closed, the closing device holders having closing devices mounted at, e.g., the distal end. The closing devices are arranged for engaging the tissue wall as the closing device holders are withdrawn.

The closing devices are preferably pointed needles that penetrate the tissue wall surrounding the aperture when the closing device holders are withdrawn. When the closing devices are engaged with the tissue wall it can be detected as a firm resistance to further withdrawal.

The closing devices are then deployed, bend further into a circular structure and draw the ends of the transversely retracted aperture together in a manner such that it closes the aperture in a straight line.

The closing devices optionally comprise a plurality of round needles of size, orientation and form such that when the closing devices are moved outwardly from inside of the aperture, the closing devices bend in an anchor like manner according to the preset memory shape of the closing devices, perforate the tissue wall and also grab tissue that is in close proximity to the wall causing the tissue surrounding the perforation to be drawn into close proximity of the closed aperture, such that the aperture can be closed and the drawn-in surrounding tissue will additionally seal the tissue closure.

The closing device, or the plurality of closing devices, can optionally be disengaged from the closing device holders and delivery mechanism, and left in place.

With the tissue aperture closed in such way, blood stasis can be achieved in a vessel by leaving the closing devices attached to the tissue wall. The closing devices may be constructed of metal, plastic or bio-absorbable material preferably having a memory material effect.

In some embodiments according to the present invention, for use in closing an aperture, incision, puncture, or other passage through tissue, communication with a blood vessel or other body lumen, a medical apparatus is suggested comprising one or more retracting units.

The retracting units have, e.g., two retracting device holders with a distal end for extending through the aperture to be closed and with a proximal end for selectively providing manipulation.

Engaging devices are captured in the retracting device holders, to be released by manipulation and positioned below the aperture to be closed. Said manipulation of said retracting device holders causes retraction of opposite sides of the aperture, causing the aperture to change the shape from a rather round aperture to a slit aperture whose extended transverse diameter (which is the longer diameter of the aperture after having retracted it) is at least double the length of the retracted longitudinal diameter (which is the shorter one) of the aperture.

In some embodiments according to the present invention, for use in closing an aperture in a tissue, a medical apparatus is suggested, the medical apparatus comprising closing members, the closing members having closing device holders with a distal end for extending through the aperture to be closed and having a proximal end for selectively providing manipulation; and having closing devices captured at the distal end of the said closing device holders to be deployed and whereby said manipulation of said closing device holders and deployment of closing devices causes the aperture to be closed.

In some embodiments according to the present invention, the medical apparatus comprises a set of retracting units.

In some embodiments according to the present invention, the medical apparatus comprises an indication for the user indicating the orientation or direction of the retracting units of the medical apparatus, e.g. being embodied as a sign, an arrow, or the like.

In some embodiments according to the present invention, the medical apparatus further includes delivery devices for delivering said closing device holder, engaging device and closing device to an operative proximity with the aperture, said delivery device being slidably connected, e.g., to said closing device holder.

In some embodiments according to the present invention, the retracting device holder comprises an elongated tube made of metal or plastic capable to capture a retracting device.

In some embodiments according to the present invention, the retracting units can be moved apart to retract an aperture.

In some embodiments according to the present invention, the retracting device holder comprises an elongated tube made of metal, plastic or other material capable to capture a retracting device.

In some embodiments according to the present invention, the closing device holder has a lateral channel at the end of the said elongated tube through which the closing device will leave the closing device holder, avoiding contact of the closing device with a structure opposite to the end of the elongated tube.

In some embodiments according to the present invention, the closing member can be manipulated to evenly distribute closing devices along the line to be closed.

In some embodiments according to the present invention, the closing devices are made of a perforating material, preferably a needle, selected from a class of material including metal, metal alloys, Nitinol, plastics, preferably having memory effect characteristics, and having a permanent or bio absorbable protective coating and being bio-absorbable.

In some embodiments, according to the present invention, the closing devices have a predetermined cross section, a proximal end and two arms each with a pointed end; both arms are the bending portion of the closing device, to expand between a first position when compressed and captured in the said closing device holder into or and a second position. The closing device is substantially linear and can be moved along the axis inside of the closing device holder in both directions in a compressed or strained state and can be released at the end of the closing device holder, returning the arms to the expanded second position with the arms having a bent shape, forming a ring with two hemi-circles or semi-circles.

In some embodiments according to the present invention, the closing devices have a preset form that allows connecting the closing devices with said closing device holder.

In some embodiments according to the present invention, the invention relates to a method for closing an aperture in a wall, incision, puncture, or other passage through tissue, communication with a blood vessel or other body lumen, in particularly, but not exclusively, the wall of a blood vessel, wherein the blood vessel has a lumen carrying blood.

It encompasses the steps:

a. retracting opposite sides of the aperture to be closed, causing the aperture to change the shape from a rather round aperture to a more slit-like aperture with a diminished diameter in axial direction to a vessel long axis and an expanded orthogonal diameter to the vessel long axis diameter, in preparation for connecting the expanded orthogonal sides of the aperture;

b. inserting and evenly deploying one or a plurality of closing devices through the aperture into the vessel lumen, the closing devices are manipulated to engage the vessel wall surrounding the aperture at the extended long sides of the aperture between the shoulders, and to connect the two expanded orthogonal sides of the retracted aperture sides and to close the aperture.

In some embodiments according to the present invention, the step of closing includes suturing, clamping or similar mechanical approximation of the engaged aperture wall.

In some embodiments according to the present invention, the medical apparatus for closing an aperture comprises features as disclosed herein, in any arbitrary combination unless not considered technically impossible by the skilled one. These and other more detailed and specific objectives and an understanding of the various embodiments of the invention will become apparent from a consideration of the following detailed description of the exemplary embodiments in the view of the drawings.

BRIEF DESCRIPTION OF THE DRAWINGS

FIG. 30A shows the closing device of FIG. 30 in a front view;

FIG. 31A shows the closing device of FIG. 31 in a perspective view;

FIG. 32A shows the closing device of FIG. 32 in a perspective view;

DETAILED DESCRIPTION OF EXEMPLARY EMBODIMENTS OF THE INVENTION

Specific embodiments of the present disclosure are directed to a vascular closing apparatus and a method for closing an aperture in a tissue such as a vascular closing device comprising a tissue retracting unit and an aperture closing member.

Tissue Retraction

In one aspect of the present invention, a retracting unit is provided to retract two opposing sites of a tissue aperture. After the two arms, sides or the like are deployed at opposite sides in the aperture to close, the distance between the arms, sides and so on is increased in order to retract the opposing sides, changing the shape of the tissue opening (aperture) to a slit, in which the two long straight sides of the aperture are approximated in preparation for the closure.

It will be appreciated by those skilled in the art, that the closure of the vessel as described herein follows the principle of surgical vascular closure techniques to prevent a narrowing or stenosis of the vessel to be treated. The retracting device is preparing the aperture in the tissue to become a transverse slit orthogonal to the vessel's long axis, comparable with an open surgical transverse suture-line. A circular retraction of the aperture, like in an open surgical cross-stitch procedure or a longitudinal suture-line is prevented to avoid stenosis of the vessel to be treated, see FIG. 27.

Aperture Closure

Another aspect of the present invention relates to a closing member to close a tissue aperture that was prepared with the retractor unit. It should be recognized that the retracting unit and the closing member might be used for general tissue repair, not just limited to vascular repair. It will be appreciated throughout the following description that the closing device of the medical apparatus can be formed of any biocompatible and/or bio-absorbable material, including, for example, Titanium (and Titanium alloys), Nitinol, stainless steel, polymeric materials (synthetic and/or natural), ceramic, etc. It will also be apparent from the description that the closing device has preferably the shape of a needle in the form of a loop or circle formed of a deformable shape memory alloy, e.g., Nitinol. As a general overview, the closing device of the present invention undergoes two positions of deformation: a first position in a compressed, straight configuration in which the closing device is captured in a closing device holder and deployed in the aperture and a second expanded round configuration in which the closing device approximates the aperture ends and closes the perforation in the tissue.

After the aperture in the tissue was prepared by the retracting device in order to form a slit, the two long sides of the slit are connected by the closing device to close the tissue opening.

Figure 1:
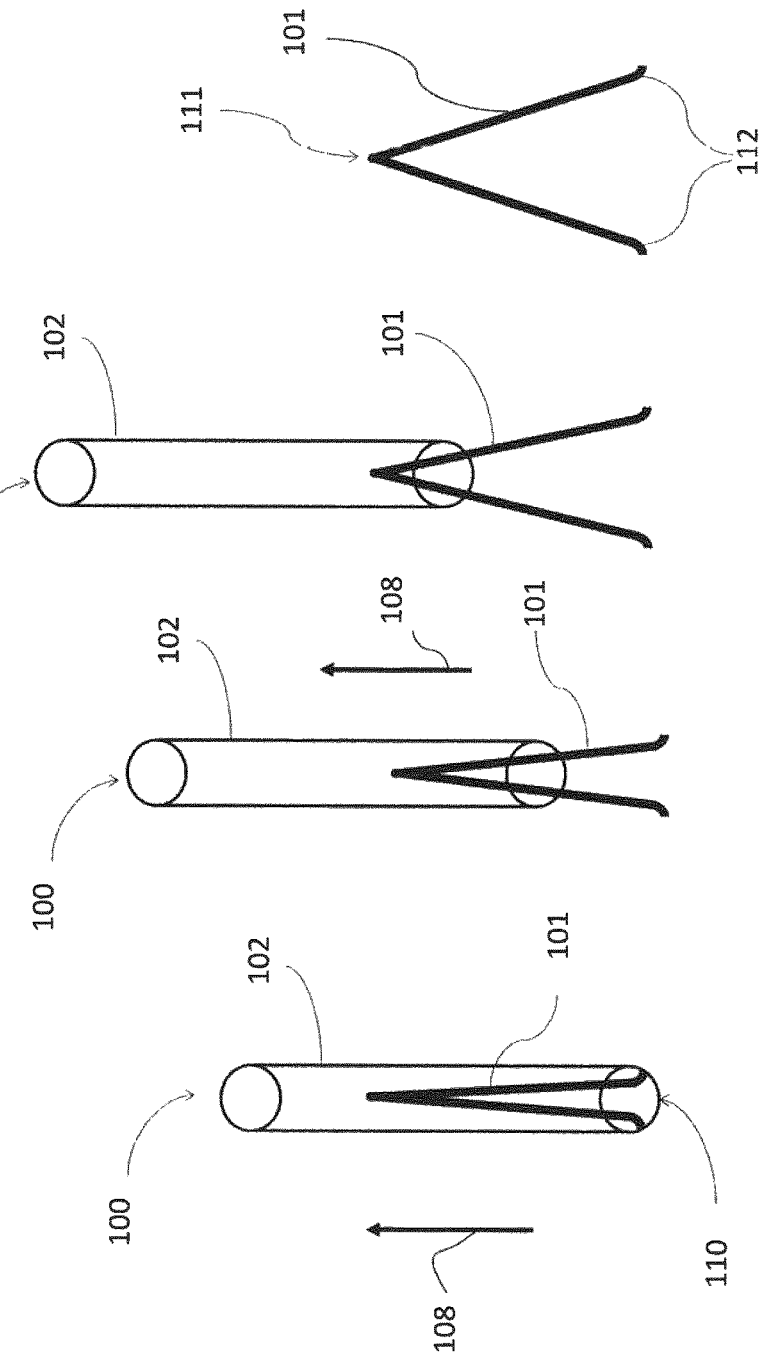
FIG. 1A to 1D are schematic side views of an embodiment of a retracting unit of a medical apparatus according to this invention.

FIG. 1 is a side view of the retracting unit 100 of this invention. The retracting unit 100 has optionally a longitudinal hollow retracting device holder 102 with a distal tip 110. A retracting device 101 is folded and is captured in the tubular retracting device holder 102. The retracting device 101 has a or one proximal end 111 and two distal ends 112. The retracting device 101 is optionally made of material with memory effect and has the ability to spread the two distal ends 112 apart like a spring. The retracting device 101 may be formed from a shape memory alloy, e.g., Nitinol, formed in the expanded stage as a triangular shape, that can be compressed in order to be captured in the retracting device holder 102. When the retracting device holder 102 is retracted along the arrow 108, the retracting device 101 is stepwise released and the distal ends 112 gradually spread due to the memory effect of the retracting device 101.

Figure 2:
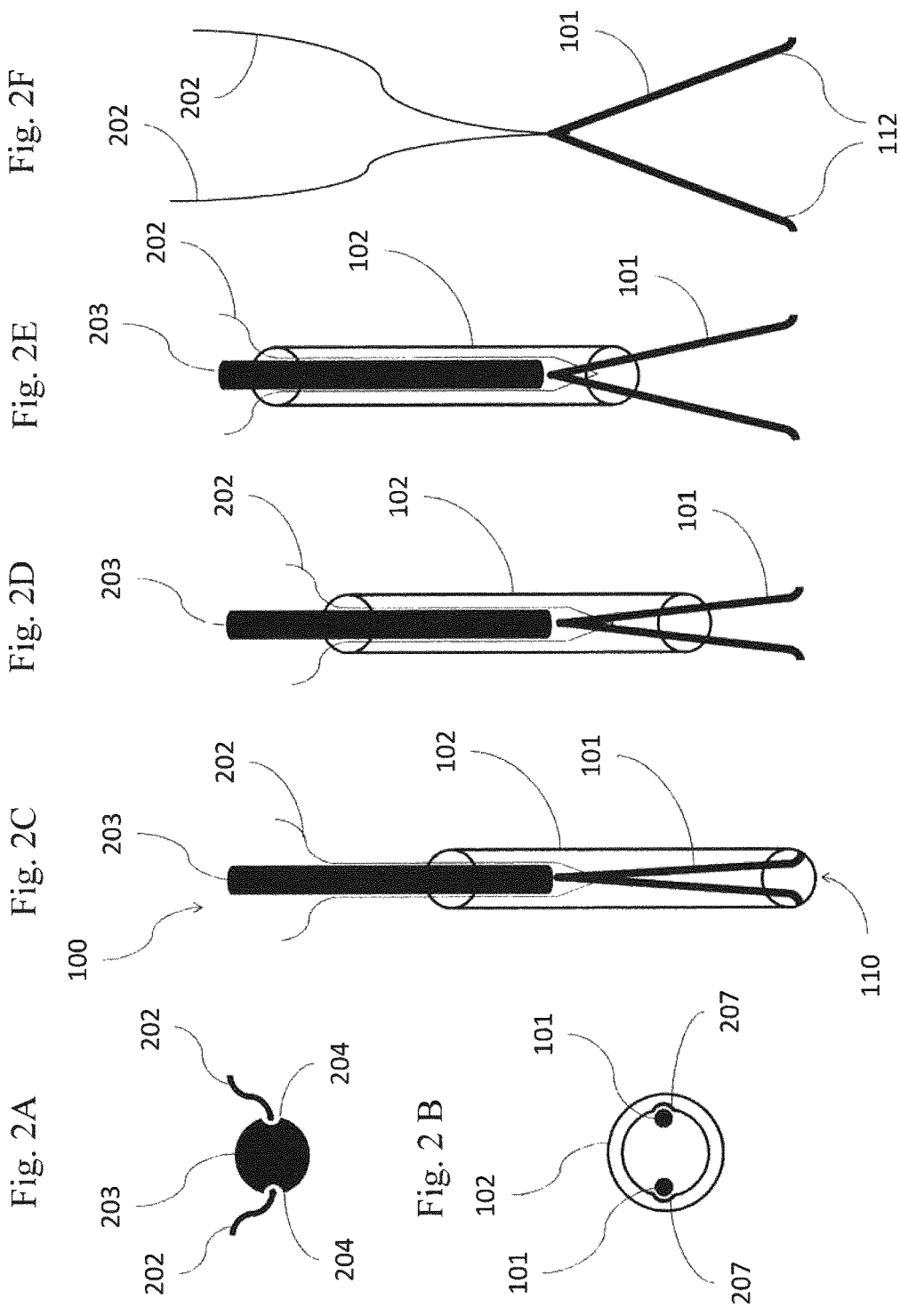
FIG. 2A to 2F are side views of an alternative embodiment of the retracting unit.

FIG. 2 is a side view of an alternative embodiment of the retracting unit 100 as shown in FIG. 1. The retracting unit 100 has a longitudinal hollow retracting device holder 102 with a distal tip 110. The retracting device 101 is folded and is captured in the tubular retracting device holder 102. In this embodiment, the retracting device holder 102 in cross-section has grooves 207 in which the arms of the retracting device 101 are captured and guided, when the retracting device 101 is moved in a longitudinal direction, in particular in the direction of the distal end of the retracting device holder 102. The retracting device 101 is pushed towards the distal end 110 of the retracting device holder 102 by, e.g., a piston 203 optionally captured in the retracting device holder 102. The retracting device 101 is looped by an optional suture 202, which tethers the retracting device 101. The piston 203 in a cross-section has grooves 204 in which the suture 202 is captured. When pushing the piston 203 in longitudinal direction from FIG. 2C to FIG. 2E, the retracting device 101 is stepwise released (FIG. 2C to FIG. 2F) and the distal ends 112 gradually spread due to the memory effect of the retracting device 101. During the longitudinal pushing towards the distal end 110 of the retracting device holder 102 or pulling away from the distal end 110 of the retracting device holder 102 by the piston 203, the retracting device 101 remains connected to the piston 203 by the tethering suture 202 or a similar acting component. Once the retracting device 101 is fully released, the retracting device holder 102 including the piston 203 may be removed, leaving the retracting device 101 still tethered by the suture 202. Later, the retracting device 101 can be removed from its position (aperture) by pulling on both ends of the suture 202.

Figure 3:
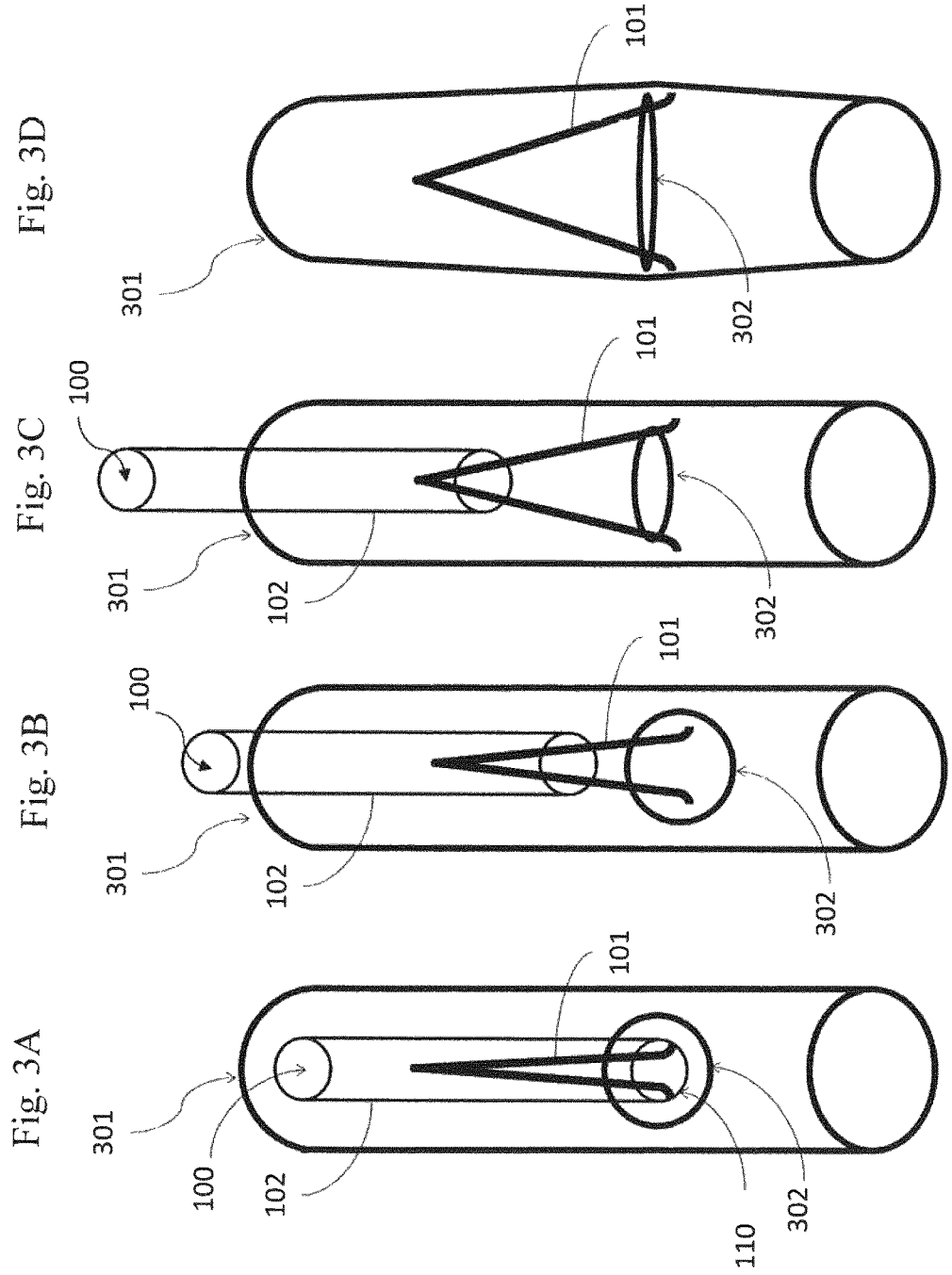
FIG. 3A to 3D are schematic, partially sectioned views of a retracting unit deployed within an aperture.

FIG. 3 is a schematic, partially sectioned view of a retracting unit 100 deployed within a vessel aperture 302.

The retracting unit 100 is developed such that it can be deployed through the wound in the patient's body through a casing which characteristically will extend from outside the patient's body with its distal end within the lumen of the vessel 301 through the aperture 302 to be closed.

The retracting unit 100 and the retracting device 101 vary in dimension according to the size of the aperture 302 and size of a vessel 301 or other body organ in a patient that is to be closed and upon the material composition of the units and devices.

The retracting unit 100 having a retracting device holder 102 and capturing a retracting device 101 is inserted in the aperture 302 of the vessel 301. Once the distal end 110 of the retracting device 101 is deployed below the vessel wall aperture 302, the retracting device holder 102 is stepwise retracted in a direction away from the vessel aperture 302 (from FIG. 3A to FIG. 3D) and the retracting device 101 is released. Due to the memory properties of the retracting device 101 the aperture 302 is gradually spread from FIG. 3B to FIG. 3D in a direction orthogonal to the vessel long axis and becomes a slit opening 302 in FIG. 3D in the vessel wall 301.

Figure 4:
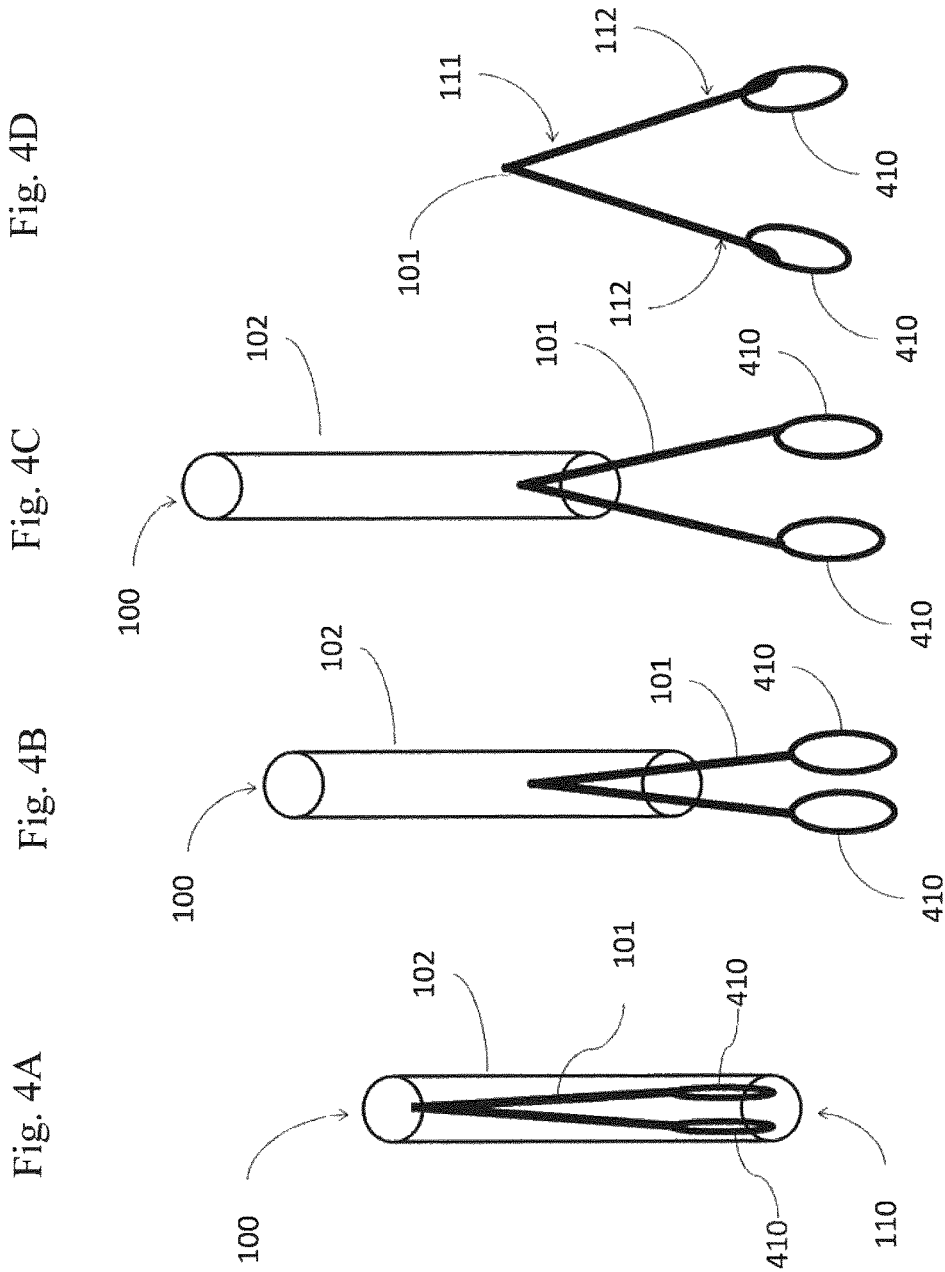
FIG. 4A to 4D are side views of an alternative embodiment of retracting unit.

FIG. 4 is a side view of an alternative embodiment of retracting unit 100 as shown in FIG. 1. The retracting unit 100 has a longitudinal hollow retracting device holder 102 with a distal tip 110. The retracting device 101 is folded and is captured in the tubular retracting device holder 102. The retracting device 101 has a proximal end 111 and two distal ends 112 with an optional engaging device 410 at each of the two distal ends 112. The engaging device 410 is preferably a looped element, preferably a wire loop, that is formed initially in an expanded state and can be folded and captured in the retracting device holder 102. The retracting device 101 is optionally made of material with memory effect like memory alloy, e.g., Nitinol and has the ability to spread the two distal ends 112 and unfold the wire loop 410. When the retracting device holder 102 is retracted along the arrows (from FIG. 4B to FIG. 4D) the retracting device 101 is stepwise released and the two arms 112 of the retracting device 101 spread and the distal engaging members 410 unfold due to the memory effect of the retracting device 101.

Figure 5:
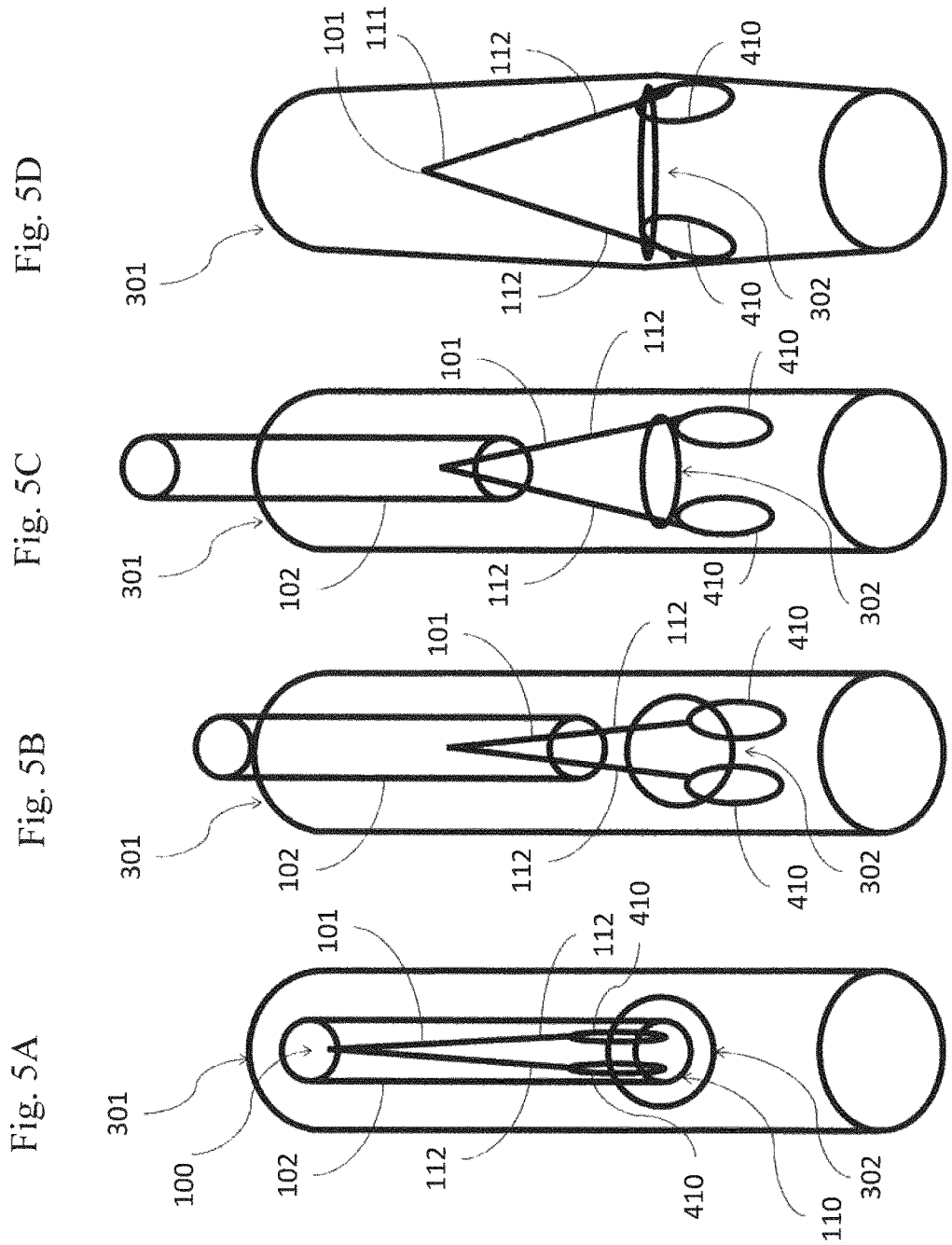
FIG. 5A to 5D are schematic, partially sectioned side views of the retracting unit deployed within the aperture.

FIG. 5 is a schematic, partially sectioned side view of the retracting unit 100 deployed within the aperture 302 of a vessel 301.

The retracting unit 100 is developed such that it can be deployed through the wound in the patient's body through a casing which characteristically will extend from outside the patient's body with its distal end within the lumen of the vessel 301 through the aperture 302 to be closed.

The retracting unit 100 and the retracting device 101 vary in dimension according to the size of the aperture 302 and size of a vessel 301 or other body organ in a patient that is to be closed and upon the material composition of the units and devices.

The retracting unit 100 having a retracting device holder 102 and capturing a retracting device 101 is inserted in the aperture 302 of a vessel 301. The retracting device 101 has a proximal end 111 and two distal ends 112 with an engaging member 410 at each of the two ends 112. The engaging member 410 is preferably a wire loop that can be folded and captured in the retracting device holder 102. Once the distal end 110 of the retracting device holder 102 is deployed below the vessel wall aperture 302, the retracting device holder 102 is stepwise retracted in direction away from vessel aperture 302 (from FIG. 5A to FIG. 5B) releasing the engaging devices 410 (FIG. 5D) that unfold below the vessel aperture 302 and engage the vessel inner wall surrounding the opening. The engaging devices 410 are further released from FIG. 5B to FIG. 5C. Due to the memory properties of the engaging devices 410 the aperture 302 is gradually spread (from FIG. 5B to FIG. 5D) and becomes a slit opening 302 (FIG. 5D) in the vessel wall 301. The unfolded engaging devices 410 prevent a retraction of the engaging devices 410 out of the vessel aperture 302 when in a slit shape.

Figure 6:
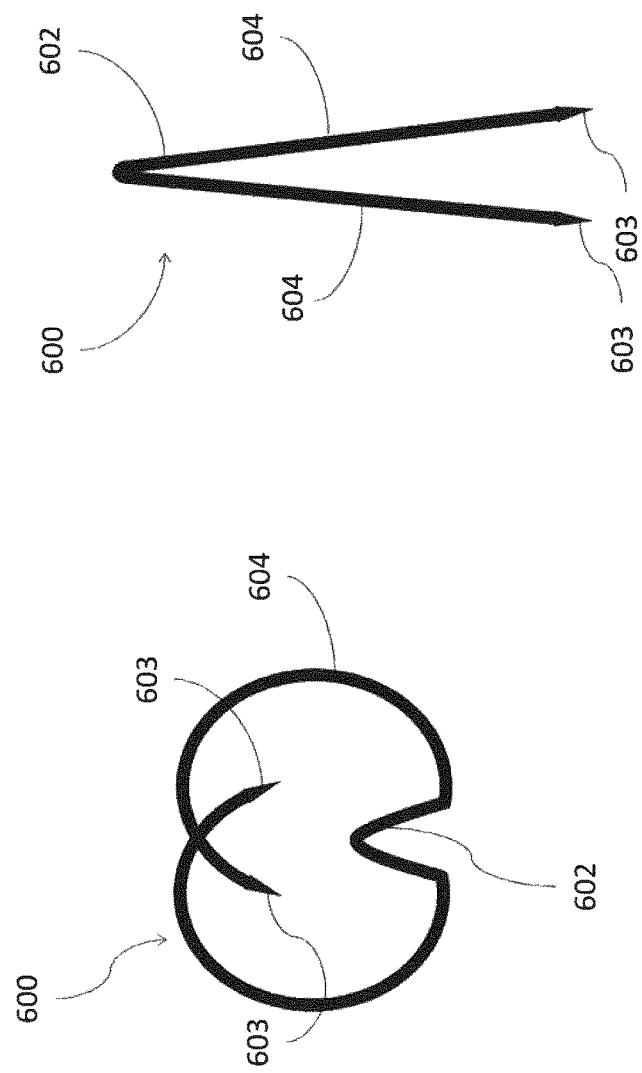
FIGS. 6A and 6B are face views of a closing device of a medical apparatus according to an embodiment of this invention in a preferred expanded round form of a needle and a compressed straight form.

FIG. 6 is a face view of a closing device 600 of this invention in a preferred form of a round needle. The closing device 600 has a proximal end 602 and first and second arms 604 with each optionally having a pointed distal end 603. Both arms 604 are the bending portions of the closing device 600.

The closing device 600 has an expanded substantially closed position (FIG. 6A) with both arms 604 forming each a hemi-circle or semi-circle in optionally or substantially one plane allowing both arms 604 to cross each other and a compressed substantially closed position (FIG. 6B) whereas the arms 604 are substantially linear allowing the closing device 600 to be captured in a retracting device holder 102 (FIG. 5) or closing member 800.

The closing device 600 can be made of various preset memory shape materials, with the material selection depending upon the particular need.

The closing device 600 may be formed of any biocompatible including, for example, Titanium (and Titanium alloys), Nitinol, stainless steel, polymeric materials (synthetic and/or natural), ceramic, etc. and/or may bio-absorbable material, for example, galvanic corrosion may be utilized. The decomposition rate may be adjusted by way of the composition not forming any macroscopic gas bubbles. The closing device 600 is preferably made of shape memory alloy, e.g., Nitinol and has the ability to form a loop like structure. The size of the closing device 600 depends upon the material composition of the needle and the required size for use. Depending on the application, the closing device 600 can have dimensions and cross-sectional dimensions ranging from 10 micro-millimeters to 10 centimeters. The size will depend on the target closure size and the size of the aperture 302 to be closed.

Figure 8:
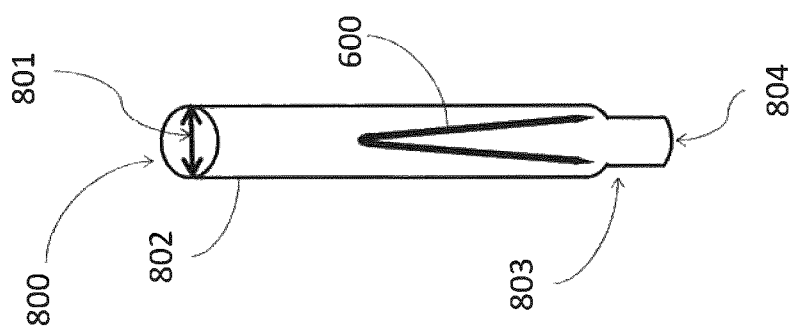
FIG. 8 is a schematic side view in longitudinal direction of a closing member containing the straight folded (being understood as compressed or not deployed) closing device captured in a closing device holder.

Preferably, the expanded looped closing device 600 (FIG. 6A) may be resiliently compressed into its compressed state (FIG. 6B), e.g., by constraining it with the closing member 800 as shown in FIG. 8.

The closing device 600 may be deployed from a contracted state (FIG. 6B) to an expanded state as shown in FIG. 6A. When in a partially expanded state, the closing device 600 can be used like an anchor to locate its position by withdrawing the partially expanded closing device 600 in the aperture 302 to be closed until the hook like formed closing device 600 perforate the wall, and further withdrawing can be detected as an increasing resistance to further withdrawal (as shown in FIG. 13F).

Figure 7:
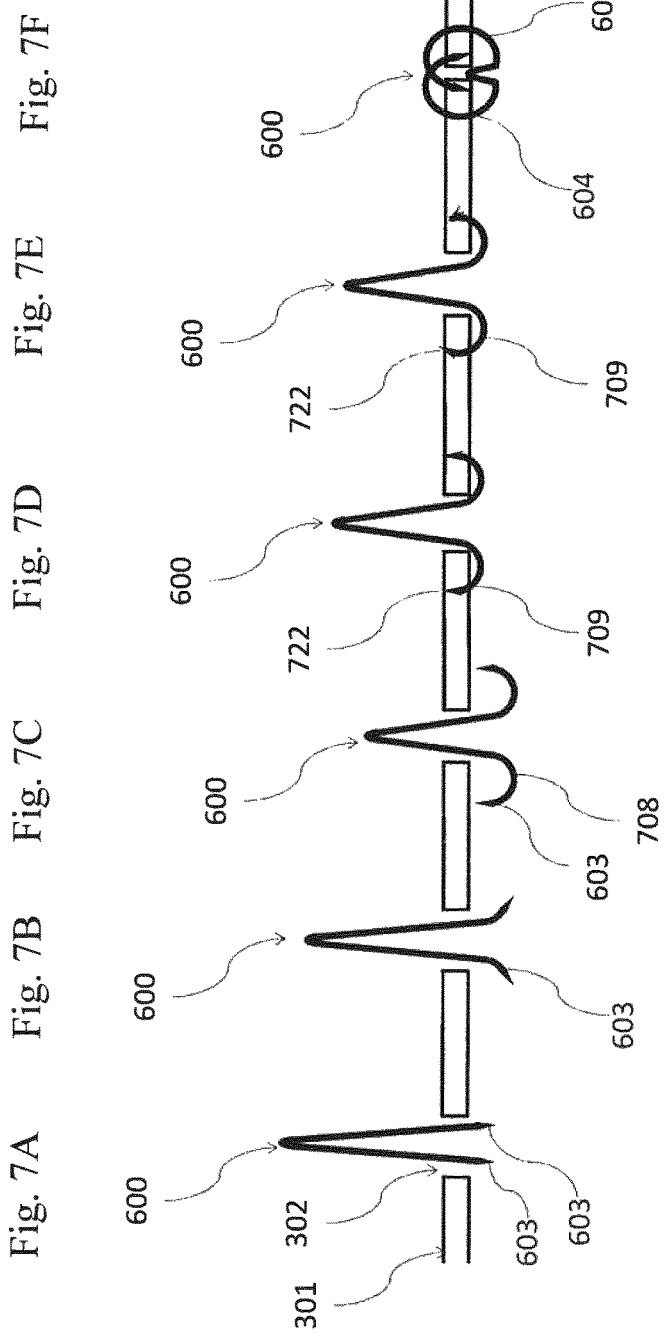
FIG. 7A to 7F are side views of a closing device as shown in FIG. 6 deployed in the aperture, penetrating the tissue and connecting the free edges of the aperture.

The closing device 600 has pointed ends 603 that will engage one side of the aperture wall surrounding the opening 302, penetrate the wall of the aperture 302 and the anchor like bent arms 604 will approximate the perforated tissue wall as shown in FIG. 7. A groove 602 in the expanded closing device 600 (see FIG. 6A) that represents the proximal end 602 of the closing device 600 in FIG. 6B allows for locking the closing device 600 to the closing member 800 as shown infra in FIG. 13.

FIG. 7 is a side view of a closing device 600 as shown in FIG. 6 deployed in the aperture 302, penetrating the tissue 301 and connecting the free edges of the aperture 302.

FIG. 7 shows the subsequent deployment of the closing device 600 from FIG. 6 in an aperture 302 to be closed.

In FIG. 7A the closing device 600 (as shown FIG. 6), is in a compressed straight configuration and advanced in the aperture 302 of the tissue 301.

In FIG. 7B the closing device 600 is partially deployed, the tip of the closing device 603 is bent due to the memomaterial effect.

In FIG. 7C with further deployment of the closing device 600 the end of the closing device 603 is bent further into an anchor form 708 with the pointed ends of the closing device 603 engaging one side of the tissue aperture 301 and penetrating (see 709) the wall 301.

The closing device 600 is then withdrawn, and the pointed ends 722 of the anchor like formed closing device 708 perforate the tissue 301. Further deployment of the closing device 600 will cause the closing device 600 to complete each of both bend arms hemi-circle or semi-circle, approximating the tissue aperture ends and closing the aperture 302.

It should be understood, however, that deployment of the closing device 600 optionally requires a closing device holder 802 as shown in the subsequent FIG. 8 to FIG. 12. It should be understood, that more closing devices 600 could be utilized depending upon the embodiment and organization of the closing devices 600.

FIG. 8 is a schematic, sectioned side view of the closing member 800 in longitudinal direction 801 comprising of a longitudinal hollow closing device holder 802 with a distal end 804. The closing device holder 802 contains the straight compressed closing device 600. The closing device holder 802 has optionally a lateral channel 803 for the deployment of the closing device 600.

Figure 9:
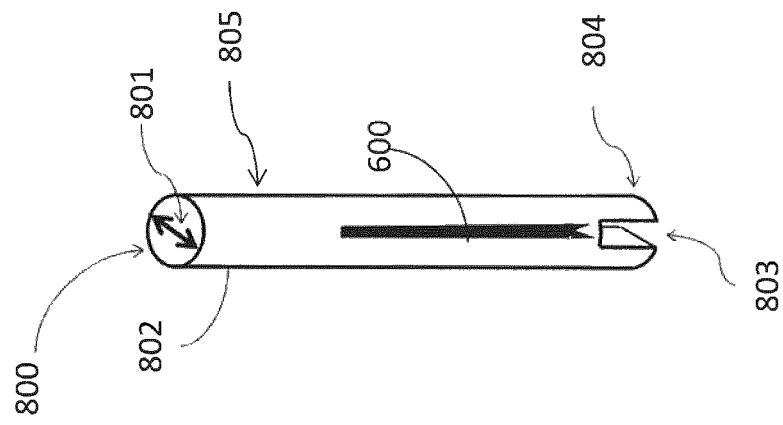
FIG. 9 is a schematic perspective view of the closing member containing the straight folded closing device captured in a closing device holder.

FIG. 9 is a schematic, sectioned perspective side view indicated by the arrow 801 of the closing device holder 802 as shown in FIG. 8, containing the straight folded closing device 600. The closing device holder 802 has optionally a lateral channel 803 for the deployment of the closing device 600. The channel 803 allows the closing device 600 to exit the closing device holder 802 in a bent way, as shown in FIG. 12B to FIG. 12D in the form of an anchor 708 (in FIG. 12C), but preventing the closing device 600 from engaging structures and tissue that might be positioned opposite to the end 804 of the closing device holder 802 like an opposite vessel wall.

Figure 10:
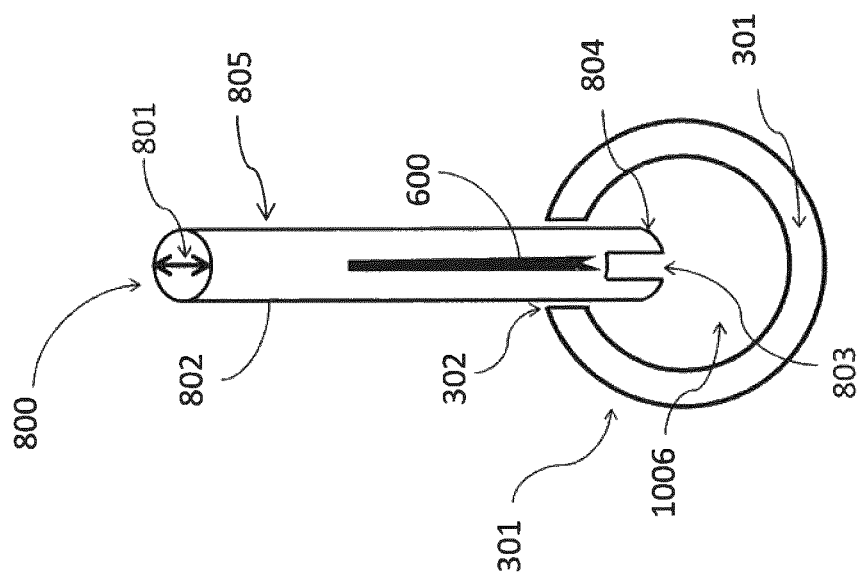
FIG. 10 is a schematic, partially sectioned longitudinal cross-section view of the closing member deployed within the aperture of a vessel.

FIG. 10 is a schematic, partially sectioned perspective view indicated by the arrow 801 of a vessel 301 and the closing device holder 802, as shown in FIG. 8 and FIG. 9, containing the straight folded closing device 600 and being advanced into a vessel lumen 1006 through the aperture 302 in the vessel wall 301. The channel 803 in the distal closing device holder 802 allows the closing device 600 to exit the closing device holder 102 in a bent way as shown in FIG. 12B to FIG. 12D in form of an anchor 708 (in FIG. 12C) preventing the closing device from engaging an opposite vessel wall 301.

Figure 11:
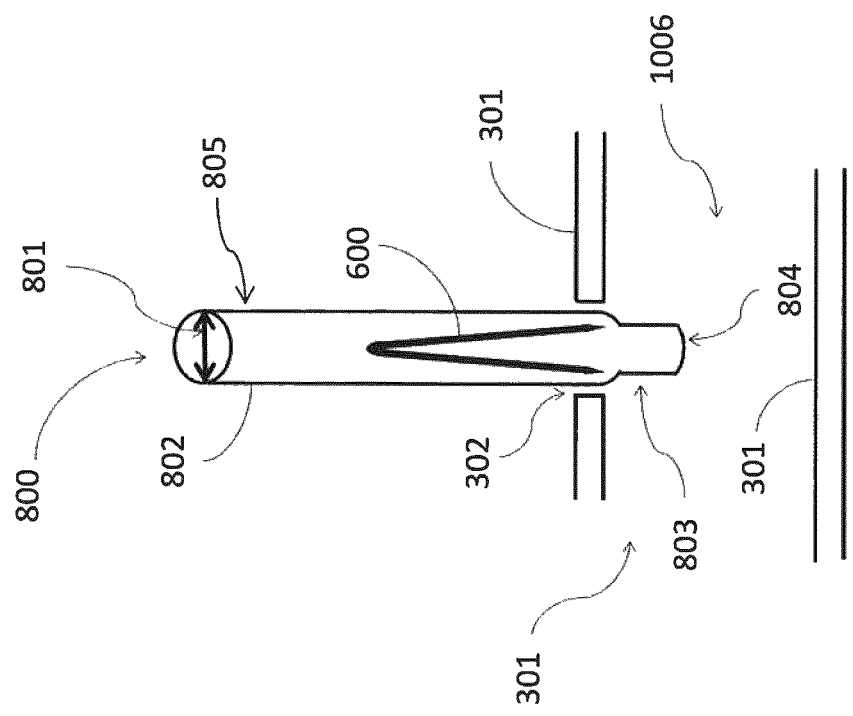
FIG. 11 is a schematic, partially sectioned longitudinal cross-section view of the closing member advanced into the aperture of a vessel.

FIG. 11 is a schematic, partially sectioned perspective view indicated by the arrow 801 of a longitudinal transection of a vessel 301 and the closing device holder 802 as shown in FIG. 8, FIG. 9 and FIG. 10 containing the straight compressed closing device 600 and being deployed in a vessel lumen 1006 through the aperture 302 in the vessel wall 301. The channel 803 in the distal closing device holder 802 allows for the closing device 600 to exit the closing device holder 102 in a bent way as shown in FIG. 12B to FIG. 12D, e.g., in the form of an anchor 708 (in FIG. 12C) preventing the closing device from engaging the opposite vessel wall 301.

Figure 12:
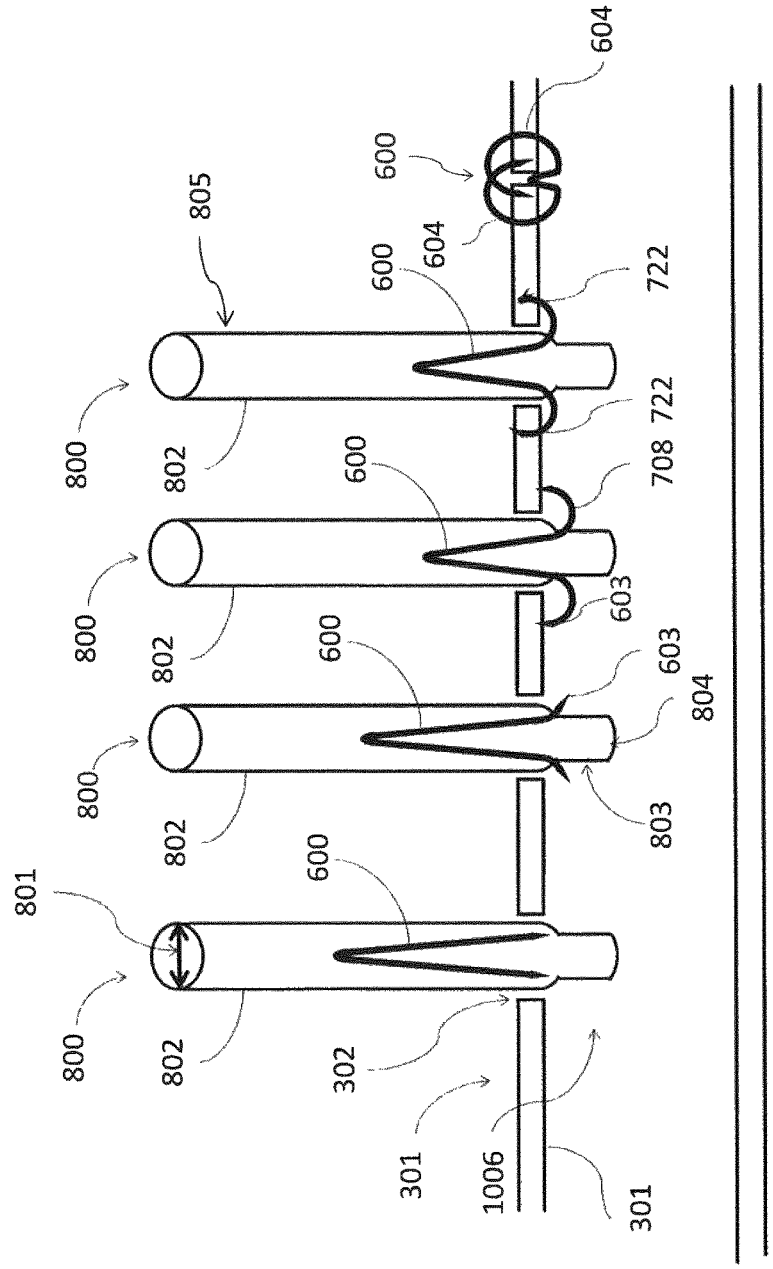
FIG. 12A to 12E are schematic, partially sectioned longitudinal cross-section views of the closing member from FIG. 10 and the closing device from FIG. 6 deployed in the aperture, penetrating the tissue and connecting the free edges of the aperture.

FIG. 12 is a schematic, partially sectioned longitudinal cross-section view as indicated by the arrow 801 of the closing device holder 802 from FIG. 8 and FIG. 9 in the sequence from FIG. 12A to FIG. 12E showing the closing device holder 802 from FIG. 8 deployed in the aperture FIG. 12A.

In FIG. 12B the closing device 600 is pushed outward in the direction of the end 804 of the closing device holder 802 and the tips of the closing device 603 bend and leave the closing device holder 802 in the channel 803.

In FIG. 12C the closing device 600 is pushed further in direction of the end 804 of the closing device holder 802, further leaving the closing device holder 802 through the channel 803 and optionally forming an anchor 708. The tips 603 of the closing device 600 are engaging the vessel wall 301.

In FIG. 12D the closing device holder 802 is further withdrawn out of the aperture 302. The anchor 603 has pointed ends perforating 722 the vessel wall 301. Further withdrawing can be detected as a firm resistance to yet further withdrawal. The closing device holder 802 is then further retracted out of the vessel aperture 302 and the closing device 600 is released. The arms 604 of the closing device 600 bend inward, pulling the ends of the aperture 302 together, closing the aperture 302 and forming a ring structure as shown in FIG. 6.

Figure 13:
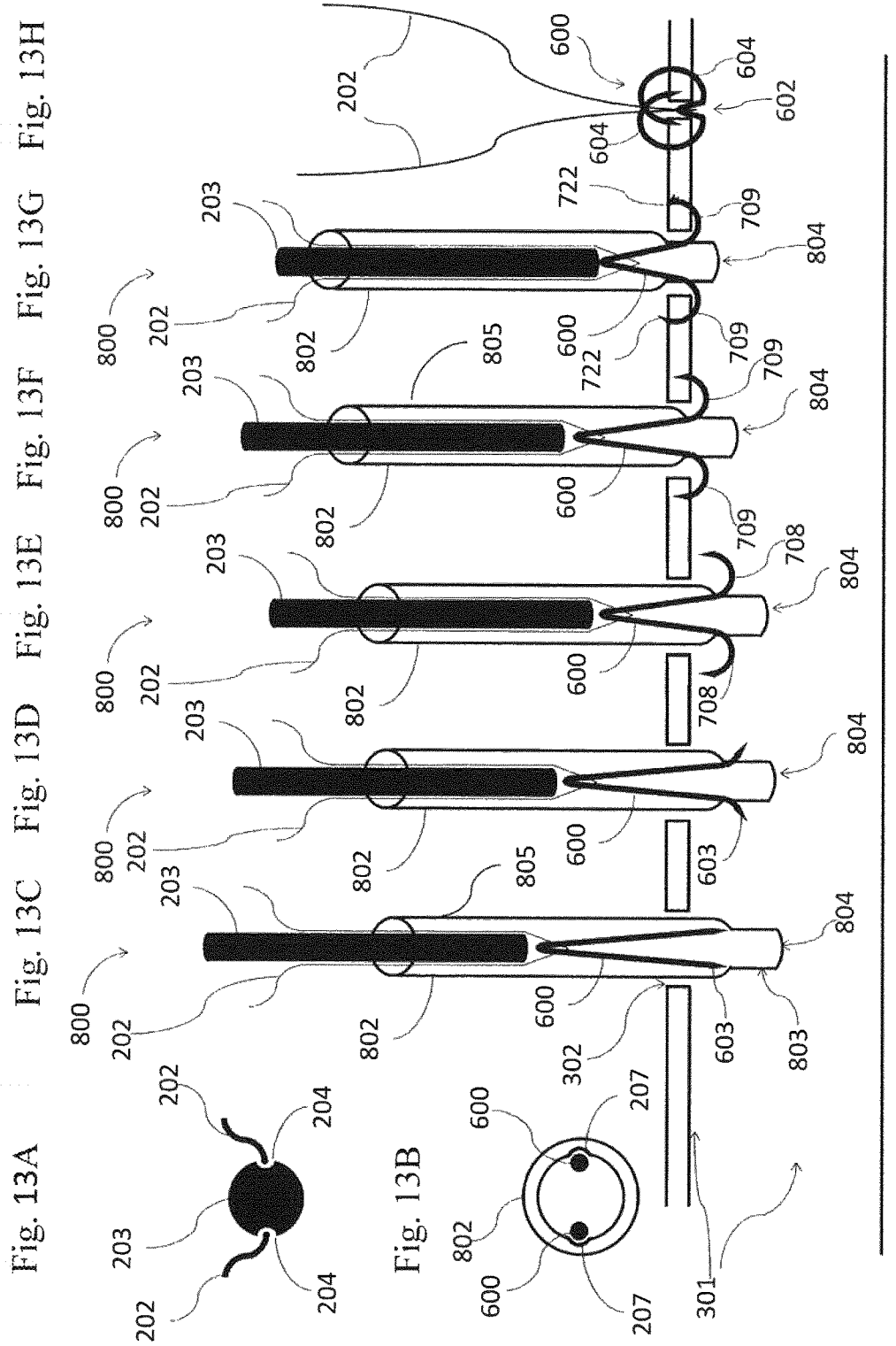
FIG. 13A to 13H are schematic, partially sectioned longitudinal cross-section views of an alternative closing member from FIG. 10 and the closing device from FIG. 6 deployed in the aperture, penetrating the tissue and connecting the free edges of the aperture.

FIG. 13 is a schematic, partially sectioned longitudinal cross-section view of an alternative closing member 800 deployed in the aperture 302 in the wall of a vessel 301. FIG. 13 shows the sequence FIG. 13C to FIG. 13H of the deployment of the closing device 600 and the closure of the aperture 302 achieved by the closing device 600. In this embodiment, the closing member 800 captures a piston 203.

FIG. 13A shows the piston 203 in cross-section, having grooves 204 in which a holding device 202, preferably a suture, is guided. The holding device 202 is tethering the closing device 600 to connect piston 203 with the closing device 600.

FIG. 13B shows the closing device holder 802 as shown in FIG. 8 in cross-section, having grooves 207 in which the arms of the closing device 600 are captured and guided, when the closing device 600 is moved in longitudinal direction, in particular in the direction to the distal end 804 of the closing device holder 802. The closing device 600 is pushed towards the end 804 of the closing device holder 802 by the piston 203 as shown in the sequence FIG. 13C to FIG. 13H.

In FIG. 13C the end of the closing member 800 is deployed in the aperture 302 in the wall of the vessel 301. The closing member 800 and the closing device 600 are oriented in the longitudinal direction of the vessel 301 as shown in FIG. 8 by the arrow 801.

In FIG. 13D the piston 203 is pushed towards the distal end 804 of the closing device holder 802 and the tips of the closing device 600 exit from the closing device holder 802 through the channel 803 and bend outwards. The holding device 202 follows the forward movement to the end 804 of the closing device holder 802 while keeping the closing device 600 and the piston 203 tightly connected.

In FIG. 13E the closing device 600 is pushed further by the piston 203 in direction of the distal end 804 of the closing device holder 802, further leaving the closing device holder 802 through the channel 804 and forming an anchor 708. The tips 603 of the closing device 600 engage the vessel wall 301 and penetrate the vessel wall 301.

In FIG. 13F the closing device holder 802 together with the closing device 600 are withdrawn, and the pointed ends 603 of the partially released closing device 600, formed like an anchor 708, perforate (see: 722) the vessel wall 301. Further withdrawing of the anchor-like shaped closing device 600 can be detected as a firm resistance to yet further withdrawal.

Further pushing the piston 203 towards the end 804 of the closing device holder 802 will cause the closing device 600 to complete with each of both arms 604 hemi-circles or semi-circles, approximating the tissue aperture ends and closing the aperture 302 somewhat like a single suture for closing the aperture 302 as shown in FIG. 13H.

Once the closing device 600 is released, the closing device holder 802 including the piston 203 is removed, leaving the unfolded closing device 600 still tethered by the holding device 202. The holding device 202 could then be utilized for localizing or even retracting the closing device 600 if needed. When the result of the closing the aperture 302 is satisfactory, the holding device 202 is removed, e.g., by pulling one arm of the holding device 202.

The following descriptions combine the retracting unit 100 and the closing member 800 in one set or medical apparatus, deployed simultaneously or subsequently. The sequence from FIG. 14 to FIG. 21 shows the closure of an aperture 302 with two closing members 800.

Figure 14:
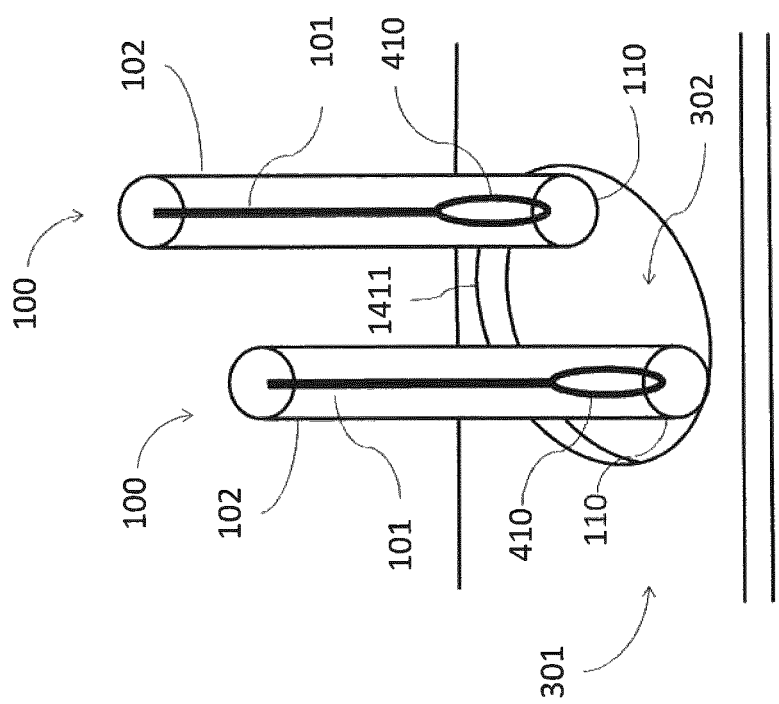
FIG. 14 is a schematic, partially sectioned perspective view of two retracting units advanced into the aperture.

FIG. 14 is a schematic, partially sectioned perspective view of an alternative embodiment of a retracting unit 100 as shown in FIG. 5. The retracting unit 100 has two retracting device holders 102 each of them capturing one retracting device 101 having distally connected an engaging device 410.

The engaging device 410 is preferably a wire loop that can be folded and captured in the retracting device holder 102.

The distal ends 110 of two retracting device holders 102 are deployed in opposite sides of the aperture 302 in a tissue 301.

Figure 15:
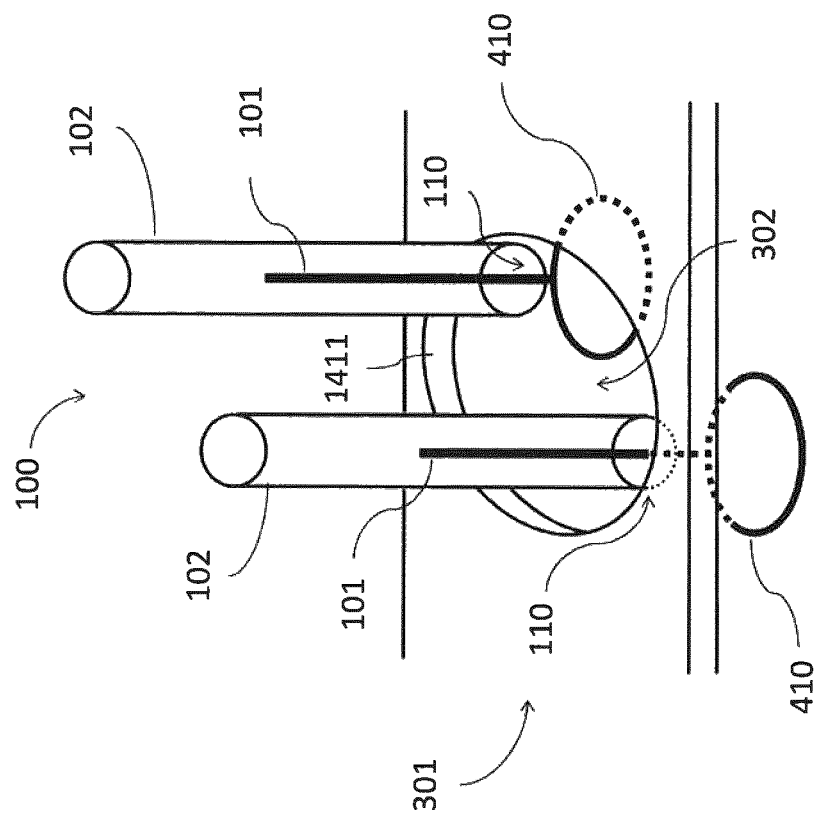
FIG. 15 is a schematic, partially sectioned perspective view of two retracting units deployed within the aperture, the two retracting devices from FIG. 4 advanced and deployed within the vessel.

FIG. 15 is a schematic, partially sectioned perspective view of two retracting device 101 in the aperture opening 302 with the ends 110 positioned on opposite sides of the aperture 302 below the aperture wall 1411. The retracting devices 101 were pushed forward to the distal ends 110. The engaging devices 410 have left the opening at the distal ends 110 of the retracting device holders 102 and the engagement devices 410 have unfolded into a loop.

Figure 16:
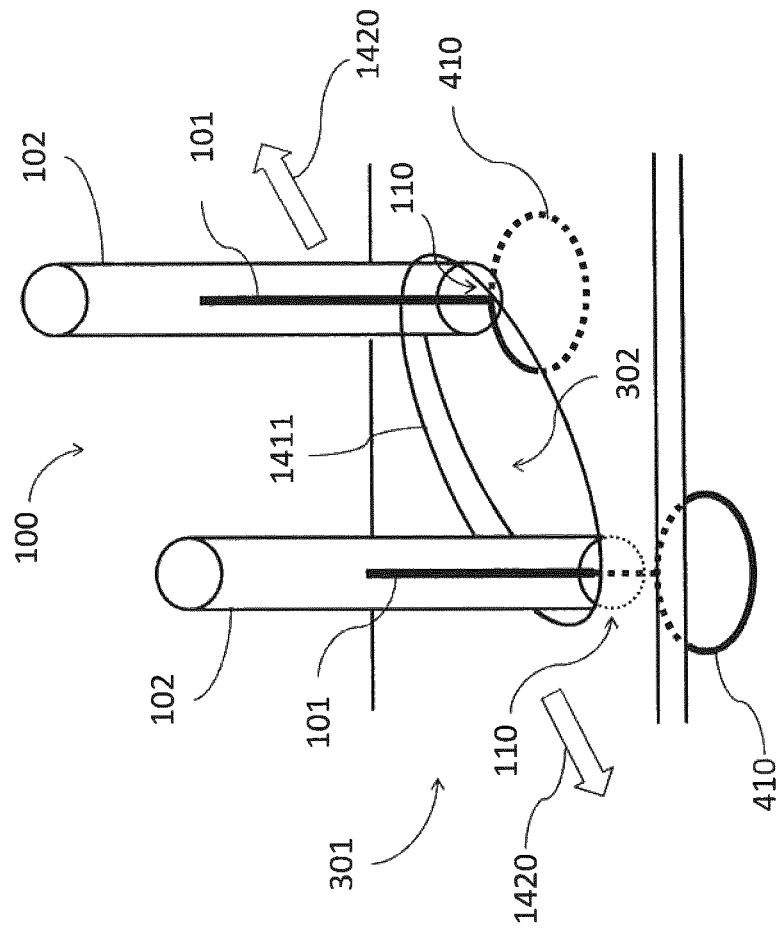
FIG. 16 is a schematic, partially sectioned perspective view of two retracting units deployed within the aperture, the two retracting devices from FIG. 4 advanced and deployed within the vessel and the aperture is retracted.

FIG. 16 is a schematic, partially sectioned perspective view of two retracting units 100 in the aperture opening 302 with the distal ends 110 positioned on opposite sides of the aperture 302 below the aperture wall 1411. The two retracting device holders 102 with the engaging devices 410 are moved in opposite direction as indicated by the arrows 1420.

Figure 17:
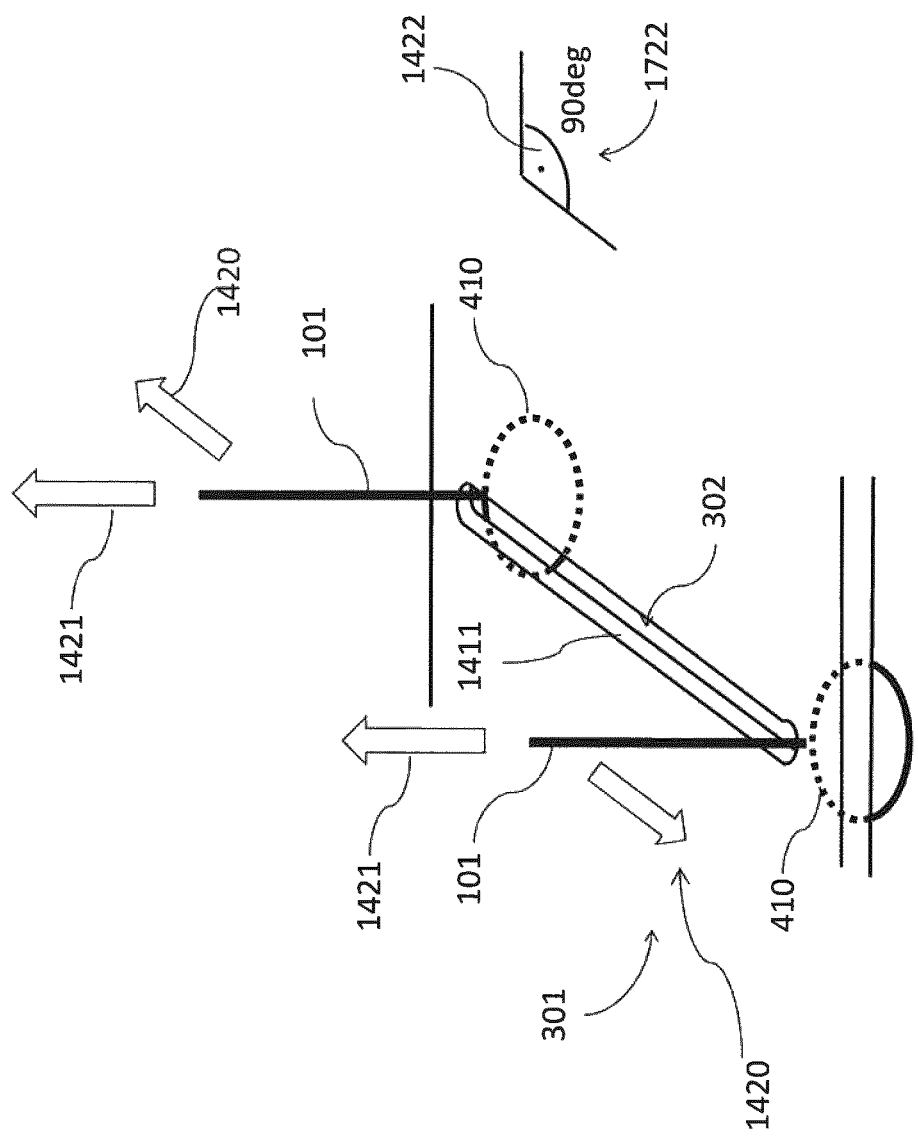
FIG. 17 is a schematic, partially sectioned perspective view of two retracting units deployed within the aperture, the two retracting devices from FIG. 4 advanced and deployed within the vessel, the two retracting devices are retracted until a stop is felt and the aperture is spread until the aperture becomes a straight slit and can be felt to stop.

FIG. 17 is a schematic, partially sectioned perspective view of two retracting devices 101, deployed in the aperture opening 302 with the distal ends 110 positioned on opposite sides of the aperture 302, below the aperture wall 1411. The two retracting devices 101 are moved in opposite direction, as indicated by the arrows 1420, causing the aperture 302 to form a slit. The opposite movement of the retracting devices 101 will come to a stop when the opening of the aperture 302 forms a straight slit, e.g., with the length of the slit being equal to half of the circumference of the aperture 302 as shown in FIG. 15. The engaging devices 410 form a loop with a diameter that is larger than the short axis of the slit opening of the aperture 302 in an angle 1422 of 90 deg to the slit opening. The engagement means 410 would lock an accidental upwards movement 1421 of the retracting units as indicated by the arrows 1420. The upward movement 1421 of the retracting devices 101 is stopped when the engagement device 410 comes into contact and cannot pass through the slit opening of the aperture 302.

Figure 18:
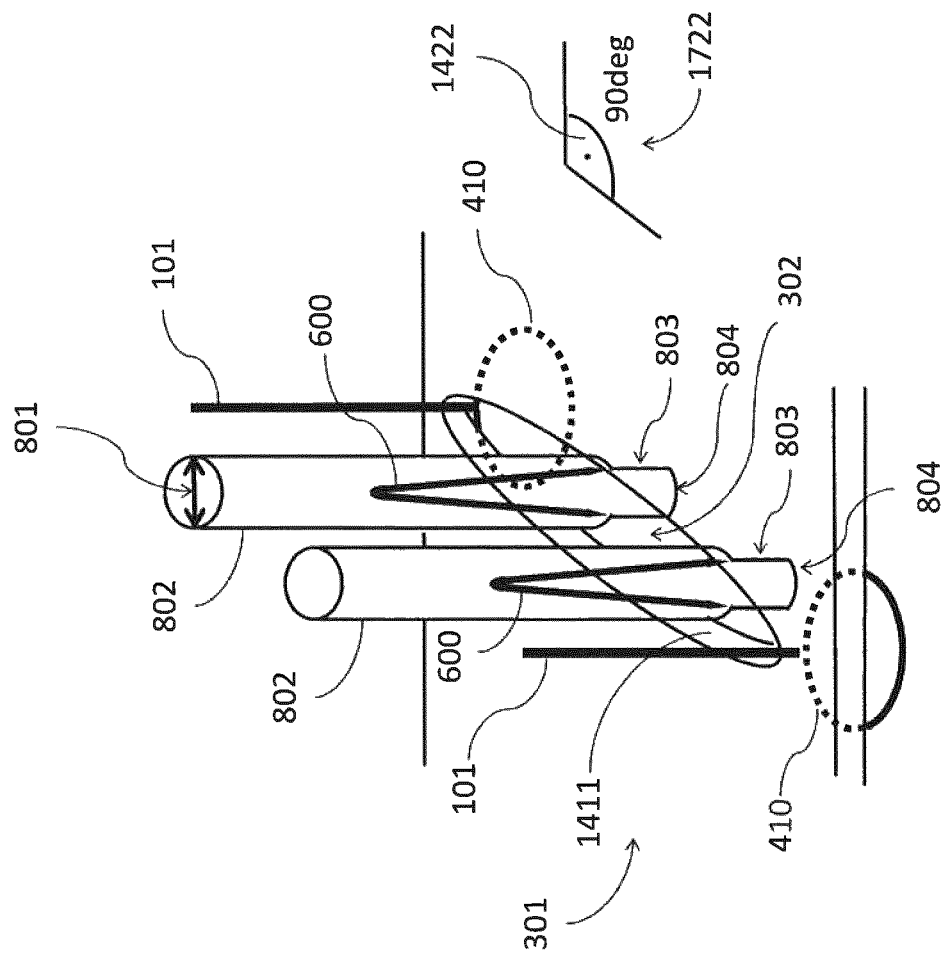
FIG. 18 is a schematic, partially sectioned perspective view of two retracting devices and two closing devices simultaneously or subsequently deployed within the aperture.

FIG. 18 is a schematic, partially sectioned perspective view of two retracting devices 101 and two engaging devices 410 deployed in the aperture opening 302 as shown in FIG. 16 having transformed the aperture into a slit form with simultaneous or sequential deployment of the closing member 800, with the two closing device holders 802 between the aperture shoulders, with the ends 804 and the channels 803 positioned below the opening of the aperture 302. The closing devices 600 are captured and compressed in the closing device holders 802 and orientated in an angle of 90 deg to the aperture opening 302 as indicated by the protractor 1722 and the arrow 801.

Figure 19:
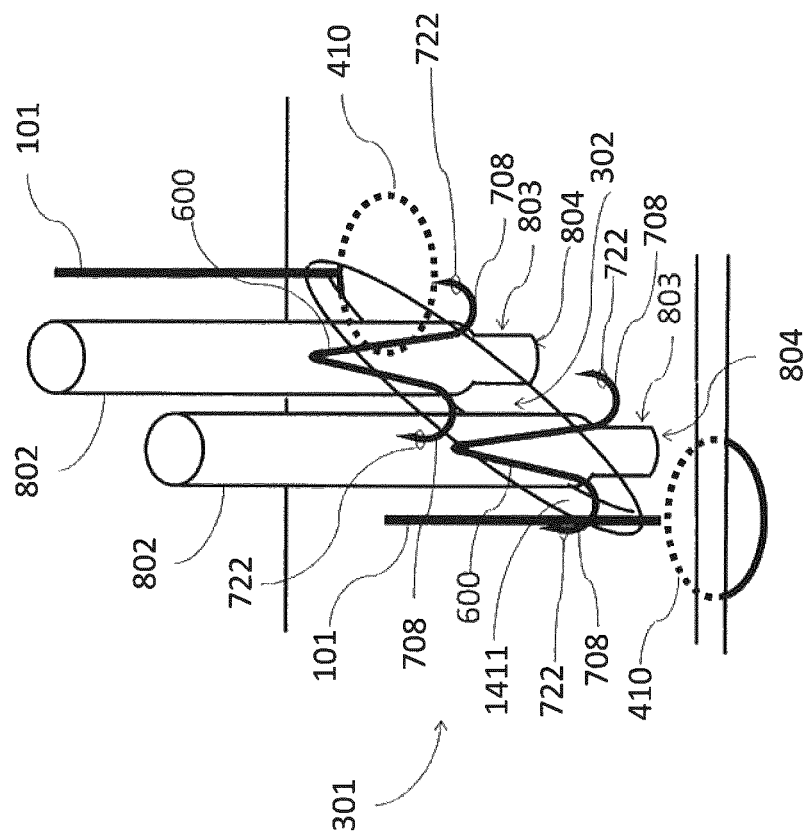
FIG. 19 is a schematic, partially sectioned perspective view of two retracting devices and two closing devices deployed within the aperture, the aperture is retracted and the aperture long edges are approached by the partially deployed closing device from FIG. 6.

FIG. 19 is a schematic, partially sectioned perspective view of two retracting devices 101 with the engaging devices 410 and closing device holders 802 deployed in the aperture opening 302 as shown in FIG. 18. The closing devices 600 are stepwise released in the direction to the closing device holder ends 804 and have left the closing device holders 802 in the channels 803, forming anchors 708 that have engaged the wall of the tissue 301, surrounding the opening 302 and the tips 603 of the closing device 600, and perforated the wall of the tissue 301 as shown at the perforations 722. Further withdrawing can be detected as a firm resistance to further withdrawal. The closing device holders 802 are then further retracted out of the vessel aperture 302, and the closing devices 600 are released.

Figure 20:
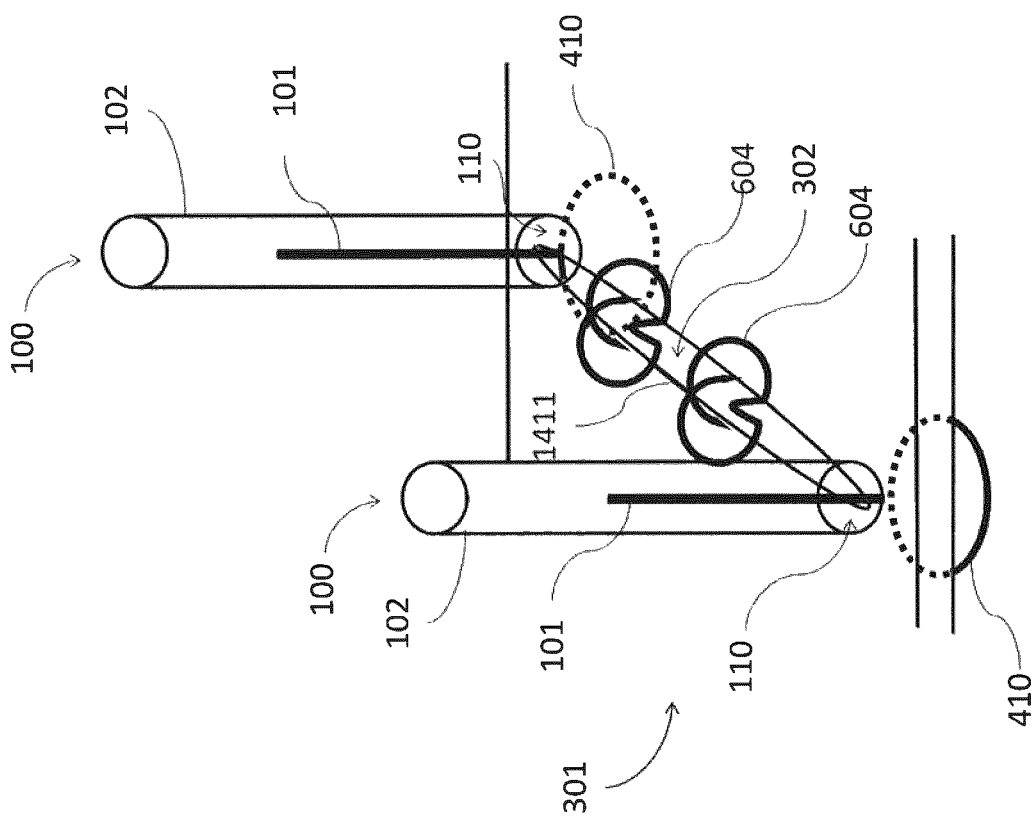
FIG. 20 is a schematic, partially sectioned perspective view of two retracting devices and two closing devices from FIG. 6 fully deployed and connecting the long edges of the aperture, the retracting units are subsequently retracted.

FIG. 20 is a schematic, partially sectioned perspective view of two retracting device holders 102, partially retracted out of the aperture 302, while the engaging devices 410 are still deployed in the aperture 302. The closing device holders 802 as shown in FIG. 19 are removed. The closing devices 600 as shown in FIG. 19 are fully unfolded forming the structure as shown in FIG. 6A. The closing devices 600 do approximate and close the aperture's 302 free edges 1411.

Figure 21:
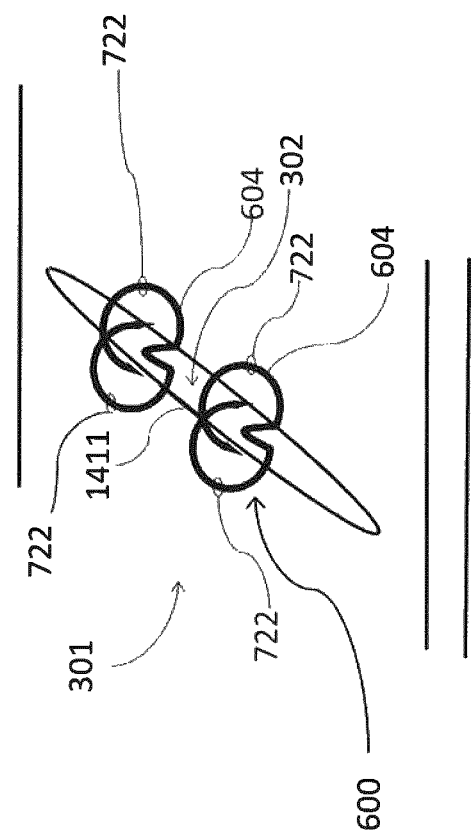
FIG. 21 is a schematic perspective view of the two released closing devices from FIG. 6 closing the aperture in a transverse line.

FIG. 21 is a schematic perspective view of the tissue 301 having a closed aperture 302. The aperture's 302 sides are approximated and closed by the closing device 600 that perforate the tissue as indicated by the perforations 722.

The following descriptions combine the retracting unit 100 and the closing member 800 in one set or medical apparatus, deployed simultaneously in a vessel 301. The sequence from FIG. 22 to FIG. 25 shows the closure of an aperture 302 in a tissue with one closing device 600.

Figure 22:
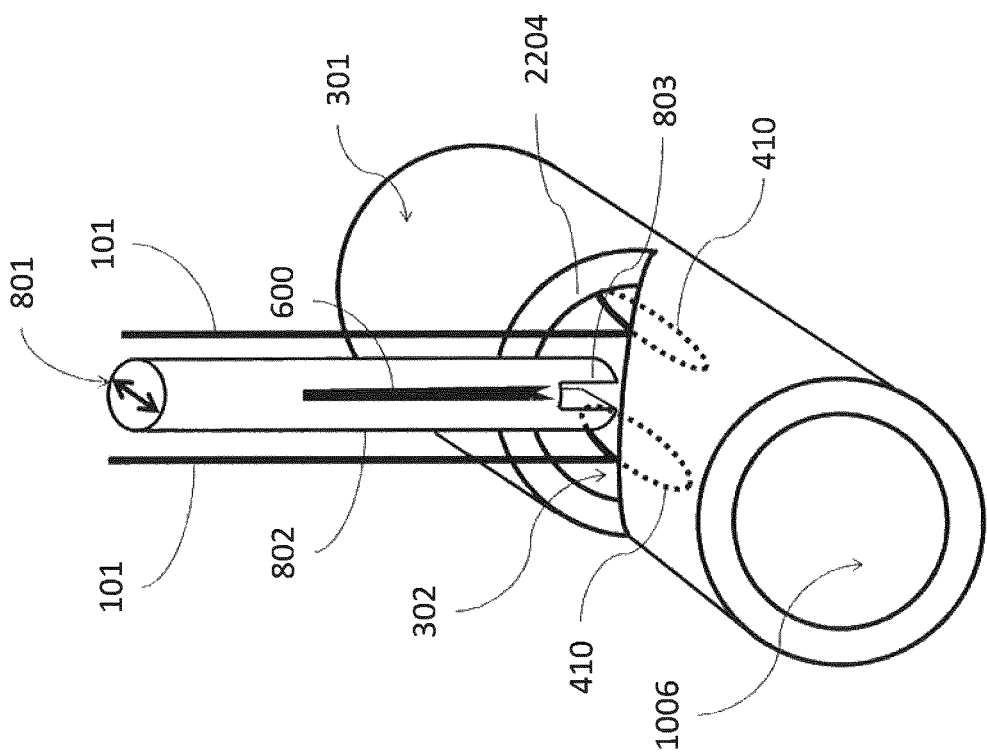
FIG. 22 is a schematic, partially sectioned perspective view of two retracting devices and one closing member simultaneously advanced into the aperture of a vessel.

FIG. 22 is a schematic, partially sectioned perspective view of two retracting devices 101, with the engaging devices 410 and one closing device holder 802 deployed in the aperture 302 in the wall 2204 of a vessel 302 within the vessel lumen 1006. The engaging devices 410 are positioned inside of the vessel lumen 1006 oriented in longitudinal direction of the vessel 301, as indicated by the arrow 801. Simultaneously, the closing device holder 802 is deployed between the retracting devices 101, with the opening of the channel 803 below the aperture wall 2204 inside of the vessel lumen 1006, oriented in longitudinal direction of the vessel 301 as indicated by the arrow 801.

Figure 23:
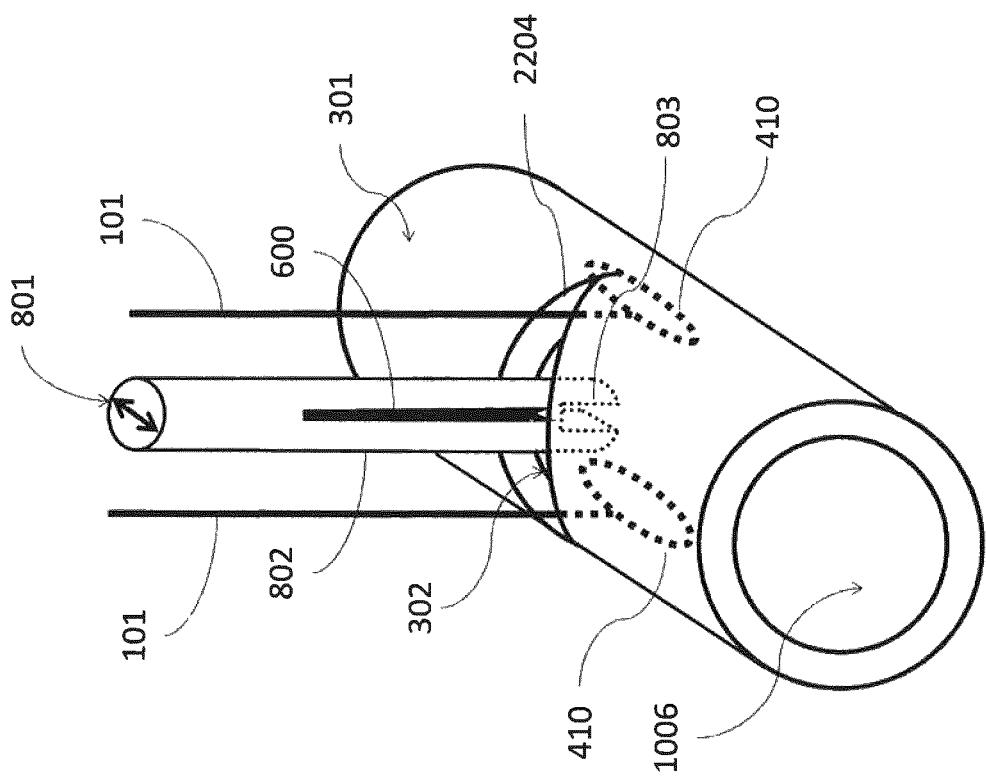
FIG. 23 is a schematic, partially sectioned perspective view of two retracting devices and one closing member deployed within the aperture of a vessel, the aperture is retracted in a direction orthogonal to the vessel long axis.

FIG. 23 is a schematic, partially sectioned perspective view of two retracting devices 101 with the engaging devices 410 and one closing device holder 802 deployed in the aperture 302 in the wall 2204 of a vessel 302. The engaging devices 410 and the channel 803 of the retracting device holder 102 are positioned below the aperture wall 2204 inside of the vessel lumen 1006. The retracting devices 101 and the engaging devices 410 are moved apart in a transverse direction which is orthogonal to the vessel's long axis. The engaging devices 410 press against the inner wall of the vessel 301 in opposite direction. This will retract the opposing sides of the aperture 302 and spread the aperture 302 of the vessel 301 in a direction orthogonal to the long axis of the vessel 301, at the same time approximating the opposing expanded long sides of the aperture 302.

Figure 24:
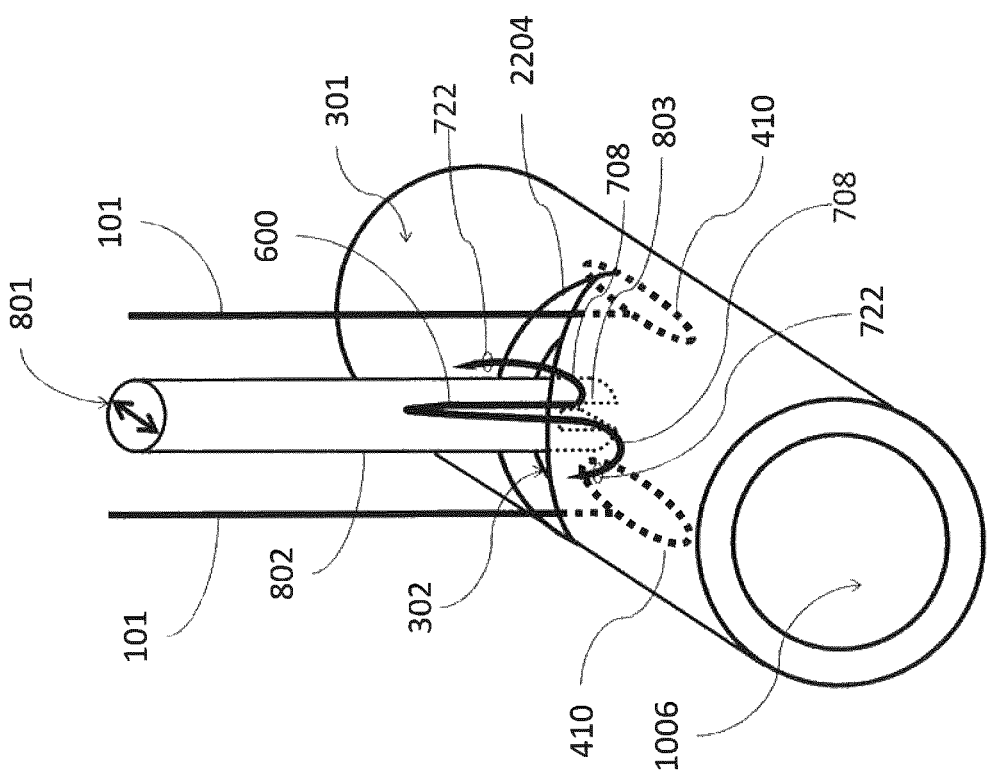
FIG. 24 is a schematic, partially sectioned perspective view of two retracting devices and one closing member further advanced into the aperture of a vessel, the aperture is retracted in a direction orthogonal to the long axis of the vessel and the aperture long edges are approached and penetrated by the partially deployed closing device from FIG. 6.

FIG. 24 is a schematic, partially sectioned perspective view of two retracting devices 101 with the engaging devices 410 and one closing device holder 802 deployed in the aperture 302 in the wall 2204 of a vessel 301. The engaging devices 410 and the channel 803 of the retracting devices 101 are positioned below the aperture wall 2204, inside of the vessel lumen 1006. The retracting devices 101 and the engaging devices 410 have retracted the aperture 302 in a direction orthogonal to the long axis of the vessel 301, causing approximation of the opposing long extended sides of aperture 302. The closing device 600 is partially deployed, has left the closing device holder 802 via the channel 803 and has formed an anchor 708 that has sufficiently grasped the vessel wall 2204 and penetrated the vessel wall 2204 as indicated by the perforation 722. Further withdrawing can be detected as a firm resistance to further withdrawal. The closing device holder 802 is then further retracted out of the vessel aperture 302 and the closing device 600 is released, forming the complete round structure, pulling the aperture wall 2204 and approximating the aperture opposing long extended sides 2204 further together. Eventually the closing device holder 802 is withdrawn and removed and the retracting devices 101 are removed by pulling the engaging devices 410 out of the closed aperture 302, while the flexible loop of the engaging devices 410 collapse and slip through the shoulders of the already closed aperture 302.

Figure 25:
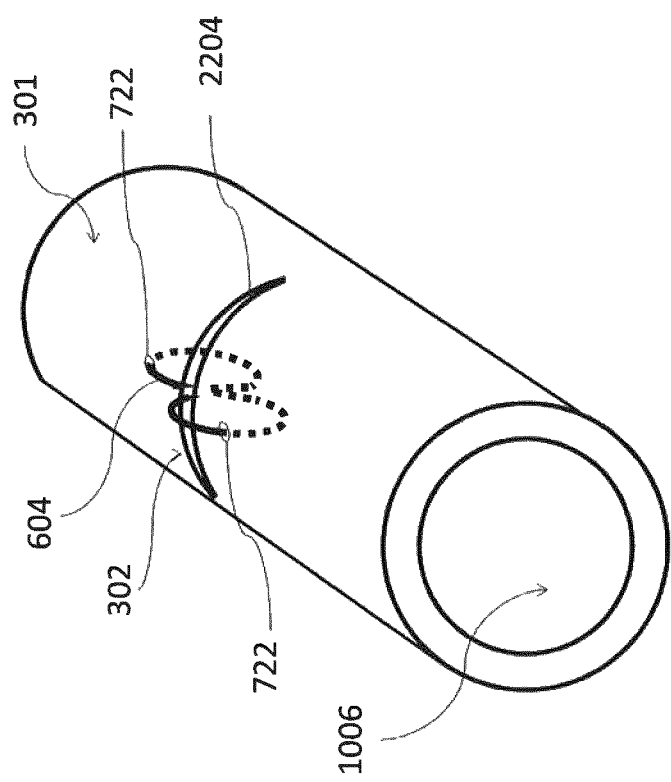
FIG. 25 is a schematic, partially sectioned perspective view of the vessel with one closing device closing the aperture.

FIG. 25 is a schematic, partially sectioned perspective view of a vessel 301 having an aperture 302 that was closed in a straight line, orthogonal to the vessel's long axis by the closing device 600 with perforations 722 of the aperture wall 2204.

Figure 26:
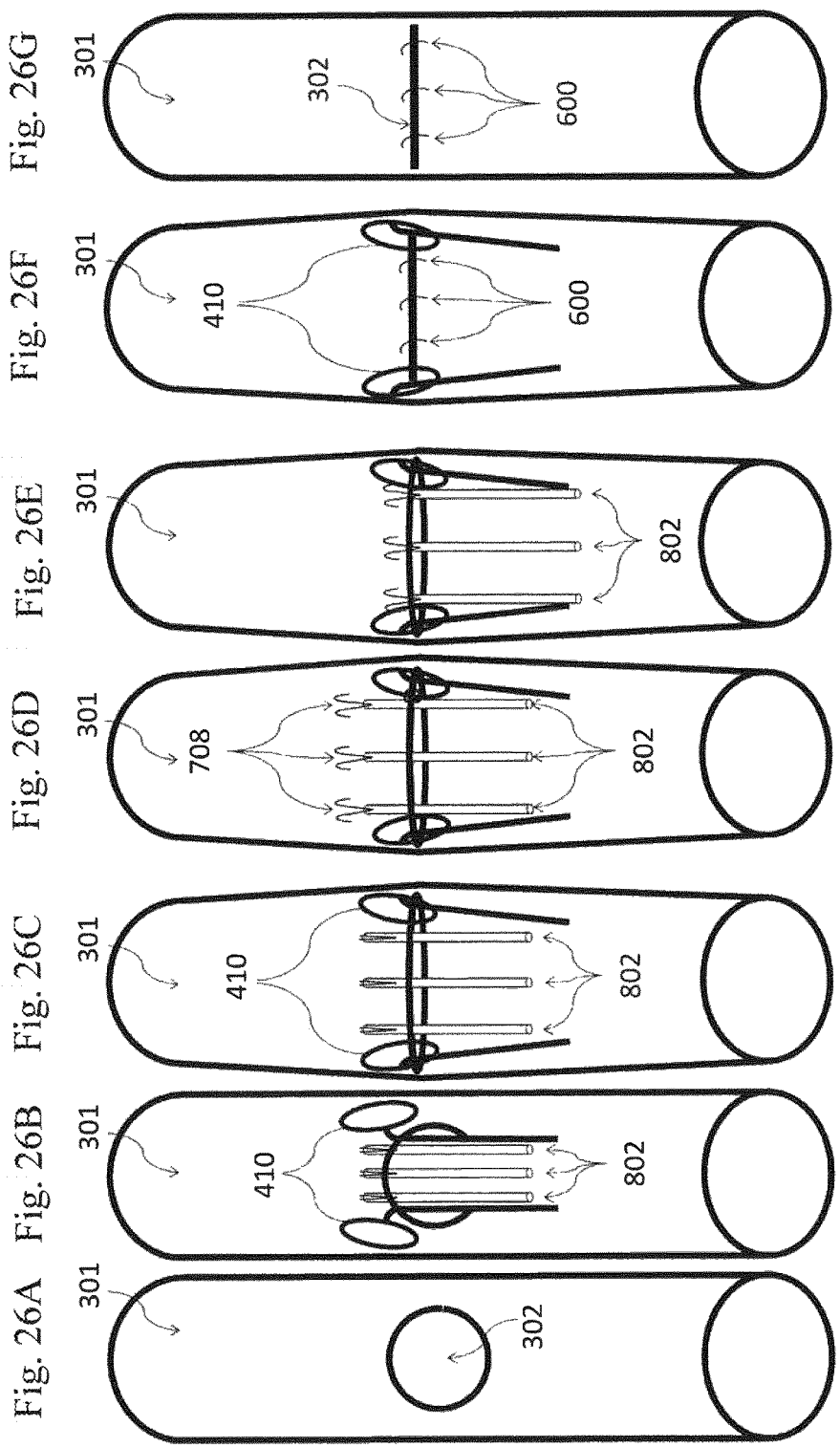
FIG. 26A to FIG. 26G are schematic, partially sectioned perspective views of the entire procedure in seven steps (a-g) of closing a vessel aperture.

FIG. 26 is a schematic, partially sectioned view from the operator's perspective showing the closure of an aperture 302 in a patient vessel.

In FIG. 26B the retracting unit 100 with two arms and the closing member 800 with three closing device holders 802 are deployed in an aperture 302 of a patient's vessel.

In FIG. 26C the engaging devices 410 are moved apart in transverse direction orthogonal to the long axis of the vessel at the opposite sides of the aperture 302, retracting the sides of the aperture 302, which results in an approximation of the upper and lower end of the aperture 302 and in forming a slit opening with two long sides, distal and proximal, and two short sides at the lateral side of the vessel. Simultaneously the closing device holders 802 are moved apart, to be equally distributed along the spread aperture 302.

In FIG. 26D the closing devices 600 are deployed and form an anchor each.

In FIG. 26E the closing device holders 802 are retracted and the closing devices 600 engage, and, upon further retracting the closing device holders 802, perforate the wall of the vessel 301 surrounding the opening 302.

Further withdrawing can be detected as a firm resistance against yet further withdrawal. The closing device holders 802 are then further retracted out of the vessel aperture 302 and the closing devices 600 are released.

In FIG. 26F the closing devices 600 are deployed forming round needles that are closing the aperture 302.

In FIG. 26G the engaging devices 410 are retracted. The closing devices 600 close the transverse seam of the aperture 302.

Figure 27:
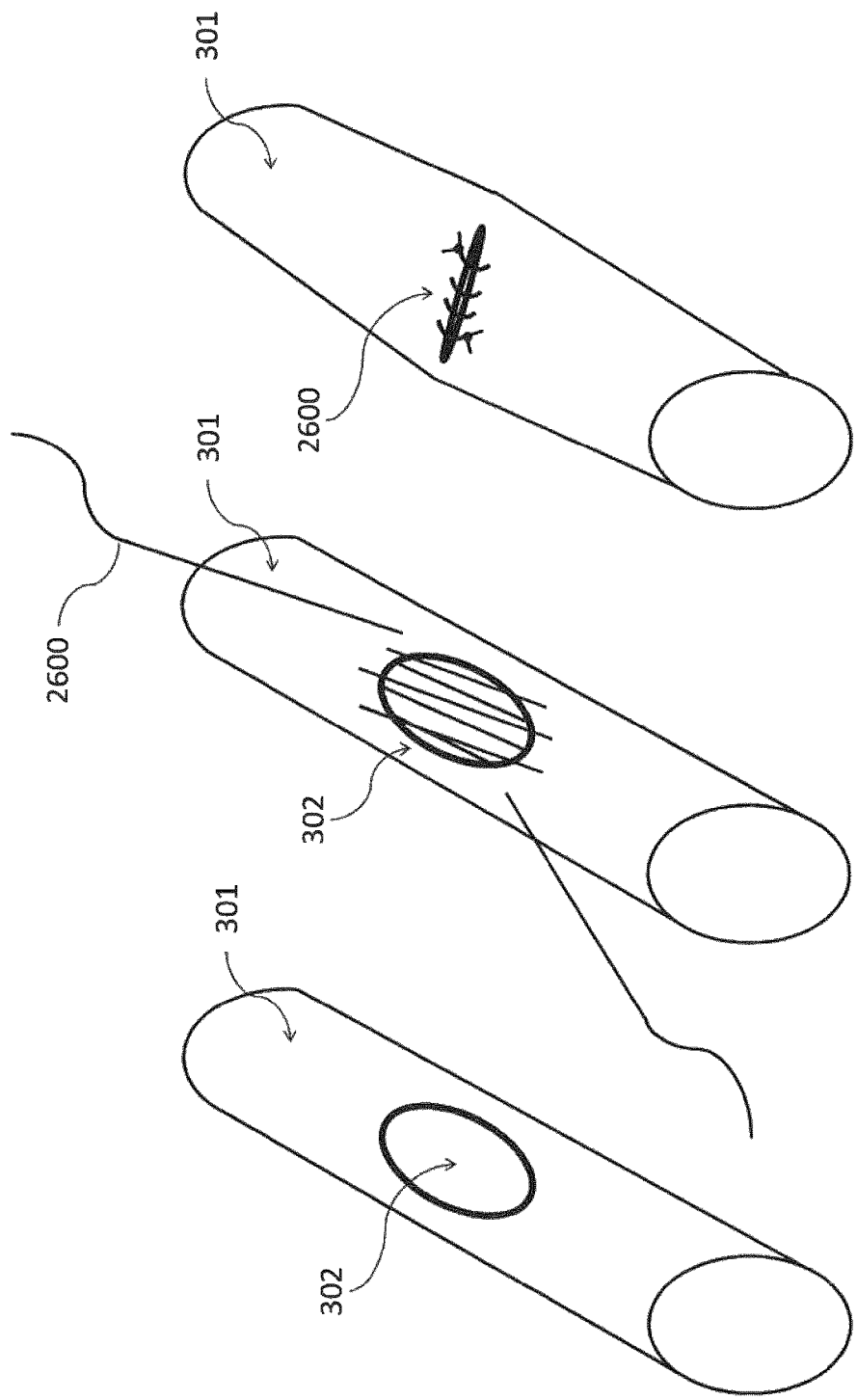
FIG. 27 shows the aperture in the patient's vessel and the closing with a transverse surgical suture.

FIG. 27 is a surgeon view of the aperture 302 of a patient's vessel 301, showing the open surgical closure of the aperture 302 with a suture. The aperture 302 in the patient's vessel 301 is closed in a straight line orthogonal to the vessel's long axis, with a running or interrupted suture 2600 to avoid a stenosis of the patient's vessel. This principle of closing an aperture in a patient vessel is of particular importance and is realized in this invention as shown in FIG. 10-FIG. 12 and FIG. 22.-FIG. 26 which illustrate an exemplary method of operating the medical apparatus.

Figure 28:
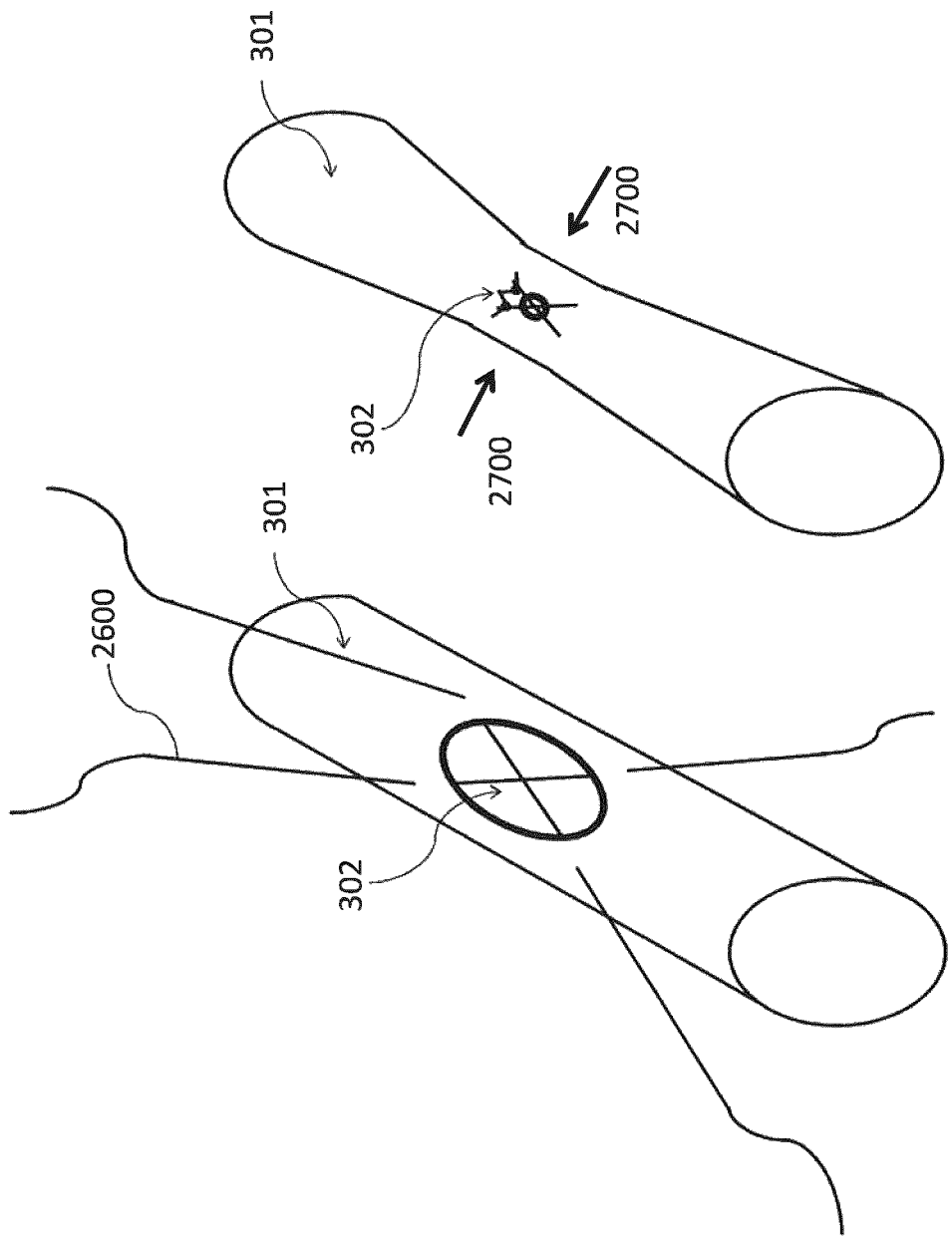
FIG. 28 shows the aperture in the patient's vessel and the closing with a cross surgical procedure.

FIG. 28 is a surgeon view of the aperture 302 of a patient's vessel 301 showing the open surgical closure of the aperture 302 with a suture 2600. The aperture 302 in a patient's vessel 301 is closed with a cross-suture or equally a purse-string suture (not shown) that approximates the lateral sides of the aperture 302. The approximation of the lateral sides of the aperture 302 is causing narrowing of the vessel lumen as indicated by the arrows 2700.

Figure 29:
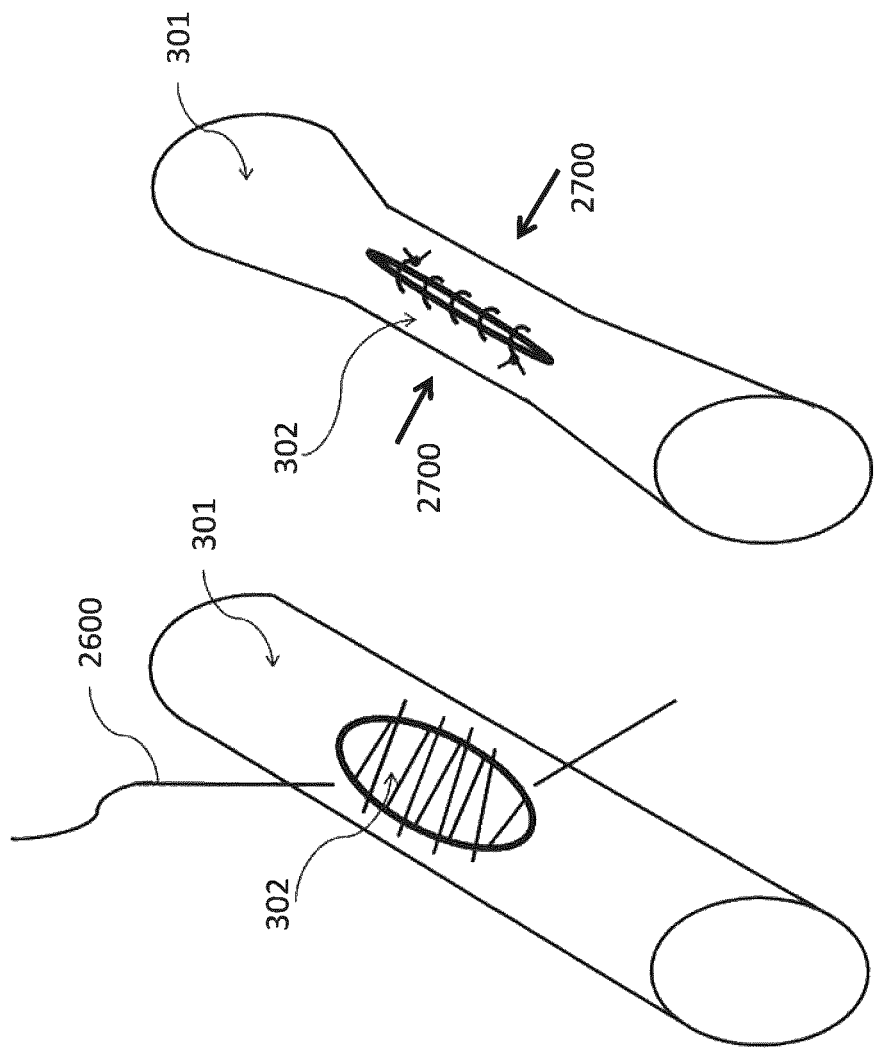
FIG. 29 shows the aperture in the patient's vessel and the closing with a longitudinal surgical procedure.

FIG. 29 is a surgeon view of the aperture 302 of a patient's vessel 301 showing the open surgical closure of the aperture 302 with a suture 2600. The aperture 302 in a patient's vessel 301 is closed with a longitudinal suture. The approximation of the lateral sides of the aperture 302, is causing narrowing of the vessel lumen, as indicated by the arrows 2700.

Only a transverse closure orthogonal to the vessel long axis like in FIG. 27, FIG. 10-FIG. 12 and FIG. 12-FIG. 26, will approximate the proximal and distal ends of the aperture 302 and at the same time spreading the transverse lateral ends of the aperture 302 avoiding narrowing of the vessel diameter and lumen.

Figure 30:
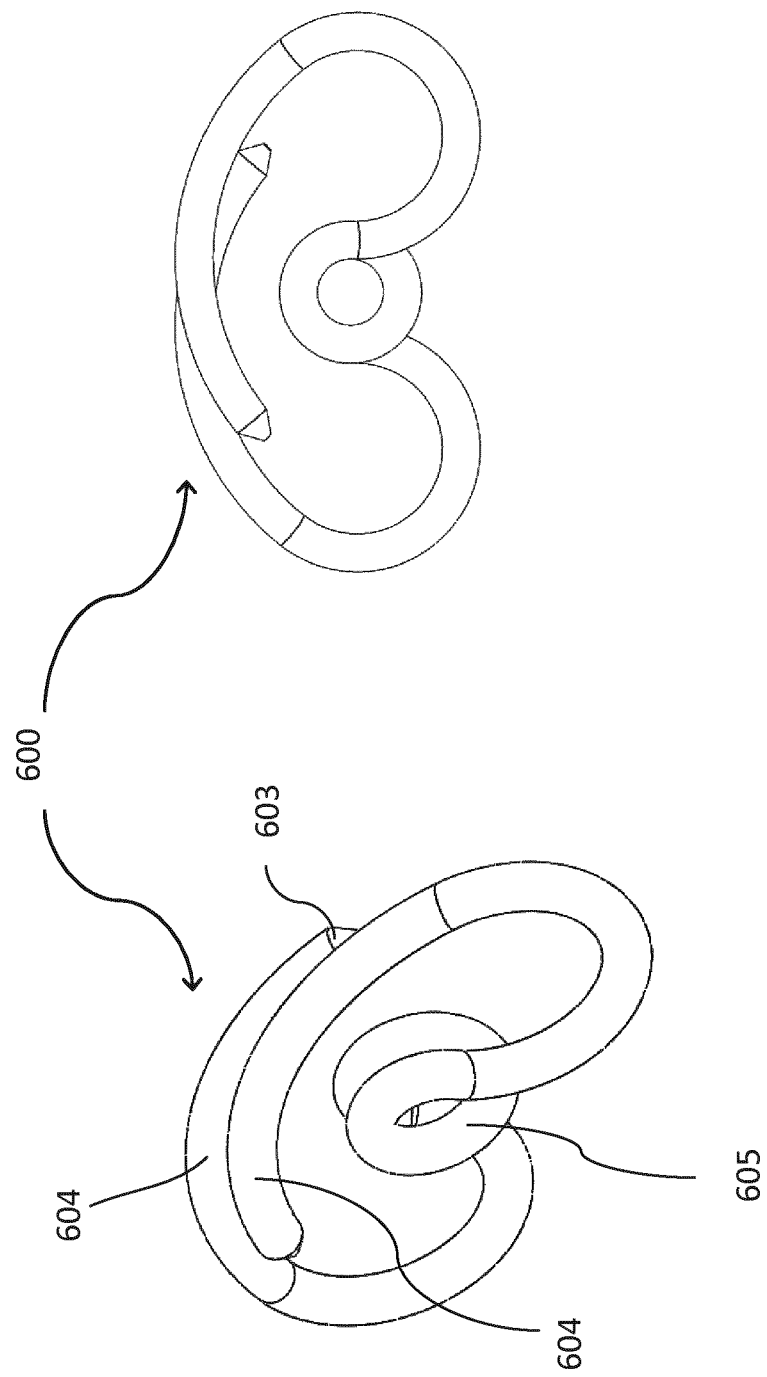
FIG. 30 shows a closing device in an embodiment in a perspective view.

FIG. 30 shows a closing device 600 in an embodiment in a perspective view. It comprises two arms 604, each of which carries an optionally pointed end 603. The arms originate from a curled or curved section 605.

FIG. 30A shows the closing device 600 of FIG. 30 in a front view.

Figure 31:
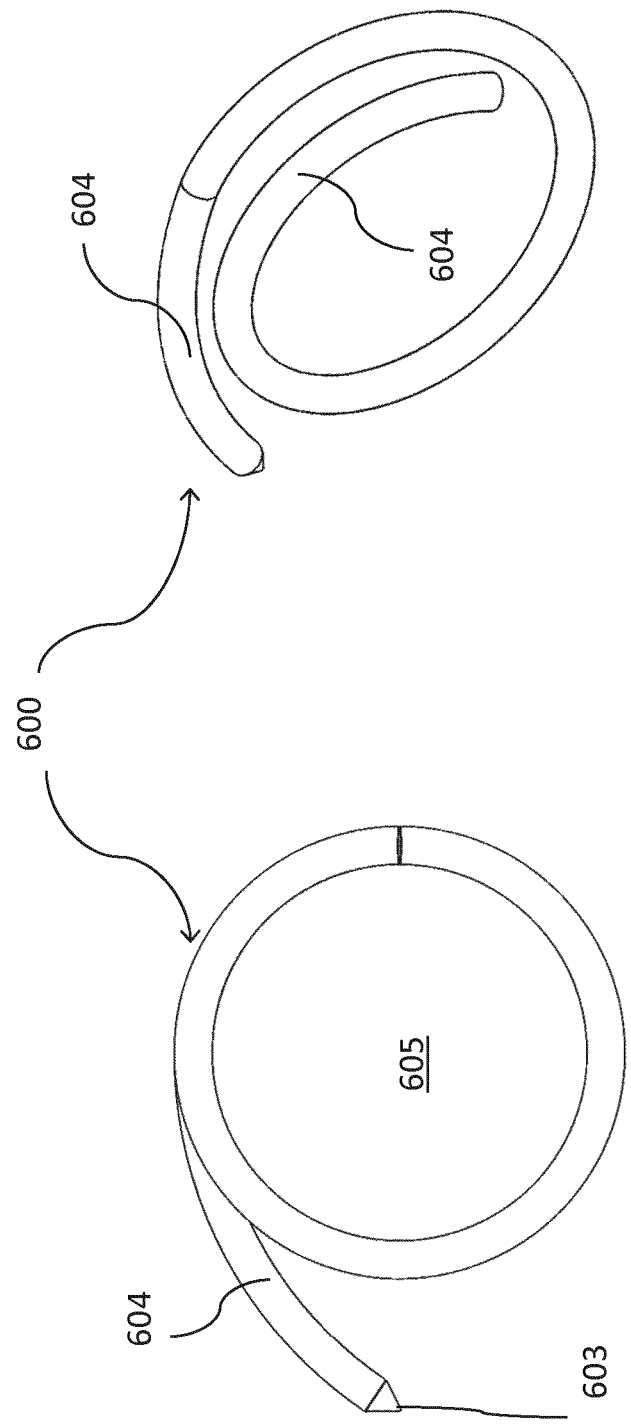
FIG. 31 shows a closing device in another embodiment in a front view.

FIG. 31 shows a closing device 600 in yet an embodiment in a front view. It comprises two arms 604, each of which carries an optionally pointed end 603. No curled or curved section is provided.

FIG. 31A shows the closing device 600 of FIG. 31 in a perspective view.

Figure 32:
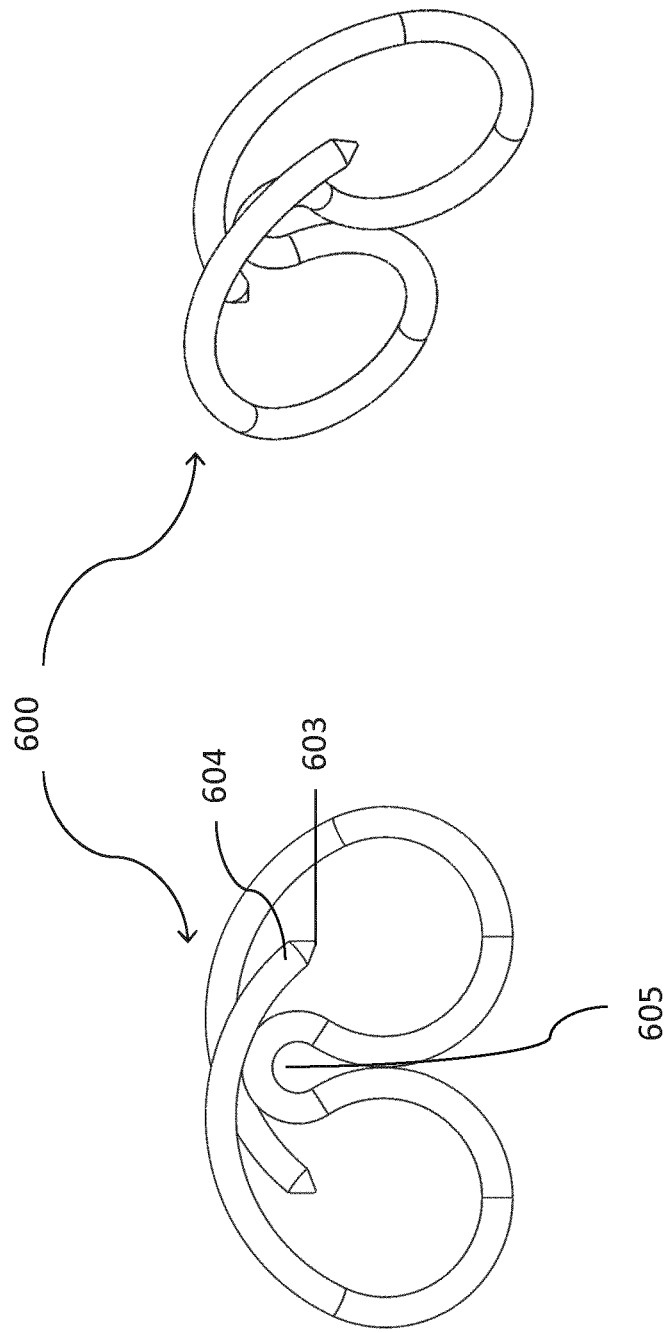
FIG. 32 shows a closing device in a further embodiment in a front view.

FIG. 32 shows a closing device 600 in an embodiment in a front view. It comprises two arms 604, each of which carries an optionally pointed end 603. In contrast to the embodiment of FIG. 30, the curled or curved section 605 is not closed, meaning that there is no spiral section.

FIG. 32A shows the closing device 600 of FIG. 32 in a perspective view.

Figure 33:
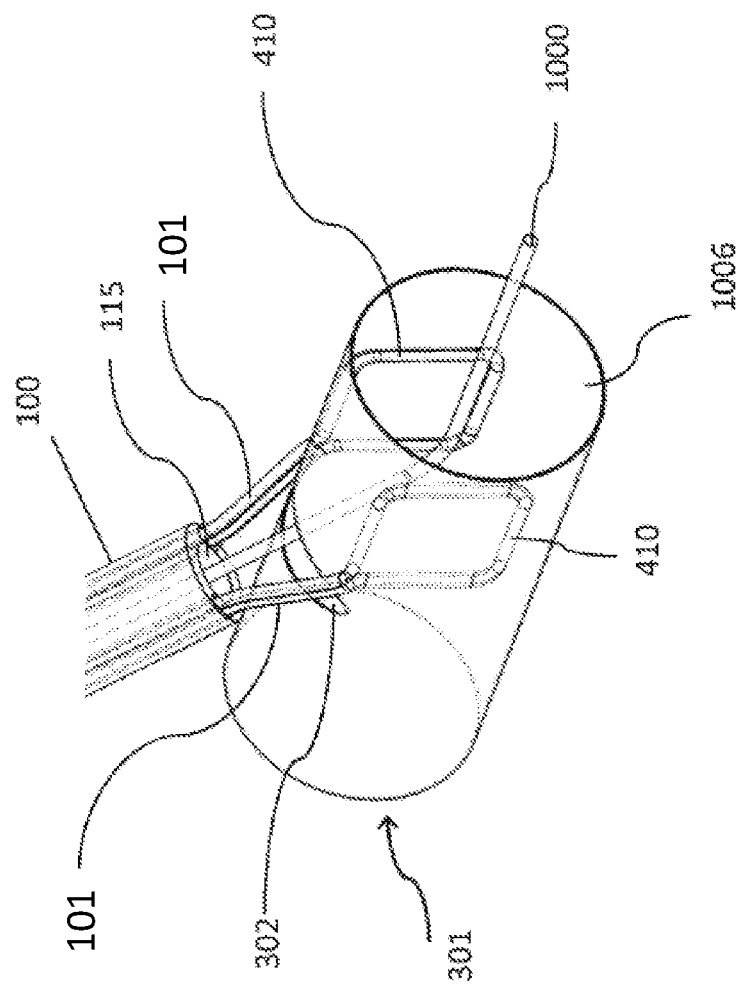
FIG. 33 shows parts of the medical apparatus according to an embodiment of the present invention in a perspective view.

FIG. 33 shows parts of the medical apparatus according to the present invention in a perspective view. A guide wire 1000 is introduced into the lumen 1006 of the vessel 301. The guide wire 1000 is run through a central opening of the medical apparatus running denoted as guide wire lumen 115.

Two engaging devices 410 retract the aperture 302 into a slit.

Figure 35:
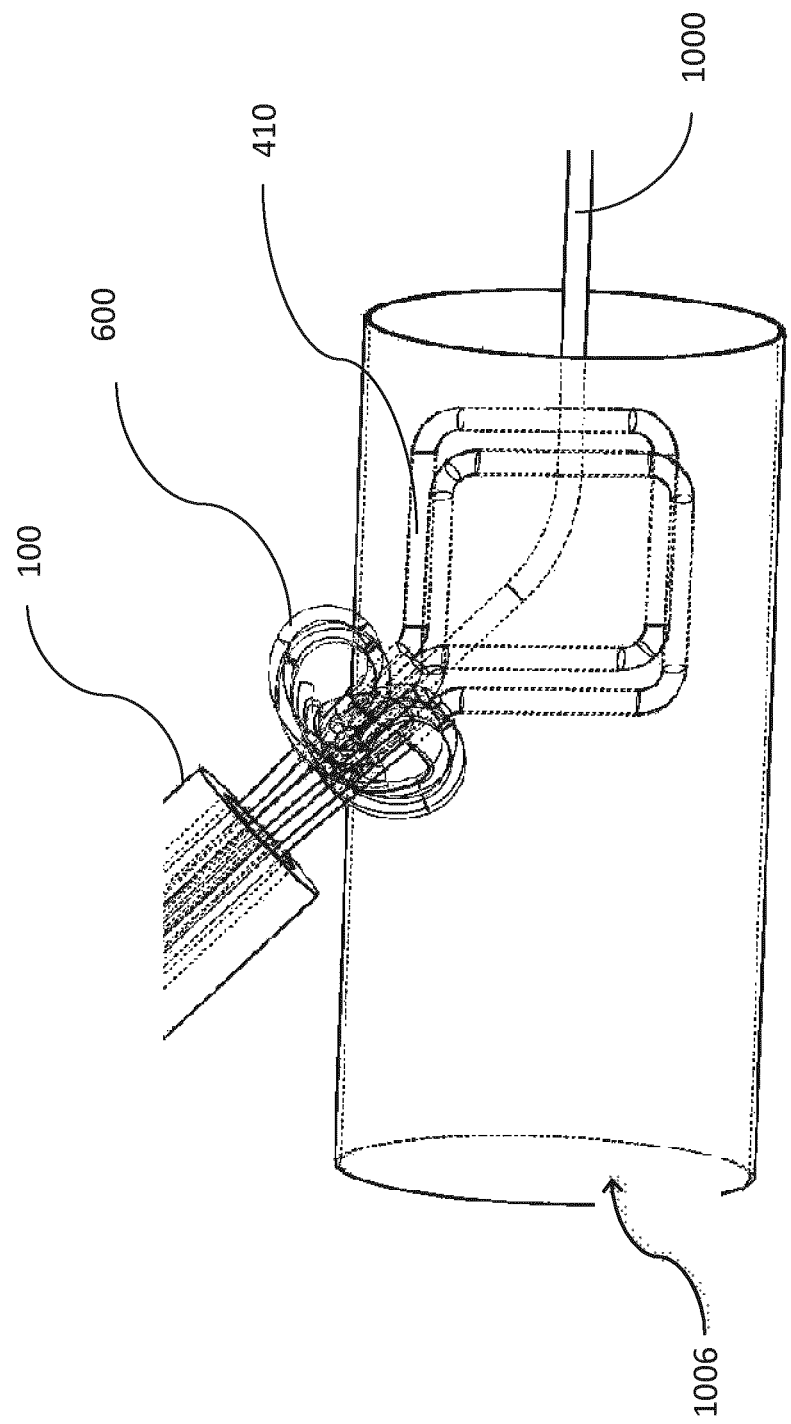
FIG. 35 shows parts of another embodiment of the medical apparatus from its side.

No retracting unit is shown in FIG. 33. If a retracting unit were shown, it could be arranged such that it can be advanced through the guide wire lumen 115, as is shown in FIG. 35 with respect to another embodiment of the medical apparatus.

Although not shown in the figures, the medical apparatus, and, in particular, the engaging device 410 or the retracting device 101 may comprise a section that hinders the guide wire 1000 to interfere with the closing device. The section may be a wire construct guiding the guide wire out or range of the closing device 600.

Figure 33A:
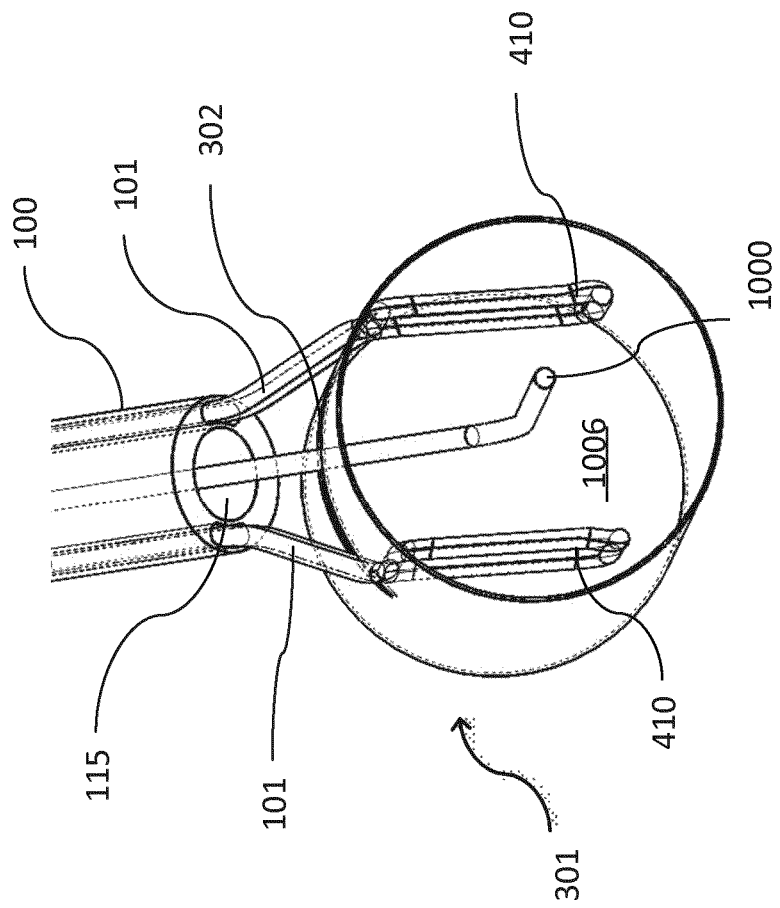
FIG. 33A shows the medical apparatus of FIG. 33 substantially from its front.

FIG. 33A shows the medical apparatus of FIG. 33 from its front.

Figure 34:
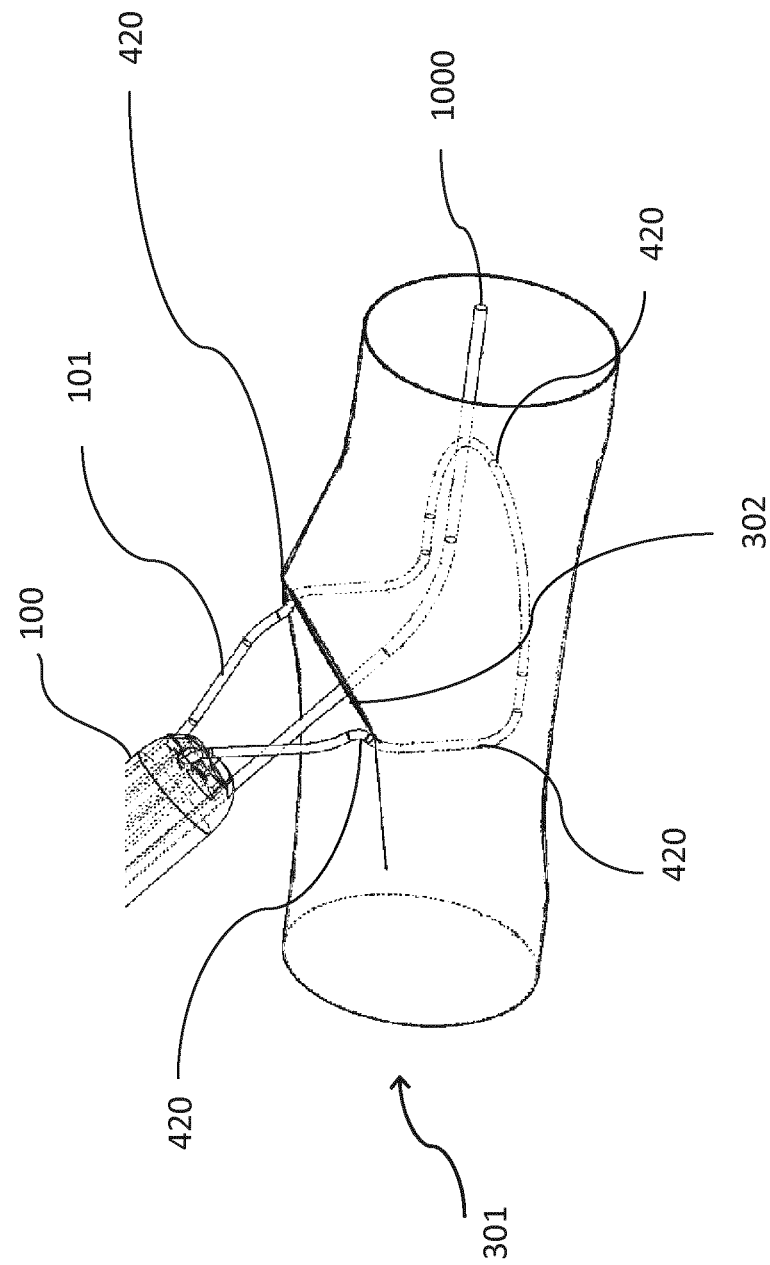
FIG. 34 shows in a perspective view a part of another embodiment of the medical apparatus.

FIG. 34 shows in a perspective view parts of another embodiment of the medical apparatus. The engaging device 410 is built from a single wire. As can be seen from FIG. 34, the retracting device 101, or any other part of the medical apparatus that is inserted into the vessel lumen in use, may in any embodiment comprise a step or a curve 420 that may interact with the wall of the aperture 302 or the vessel 301 such that it gives tactile feedback to the surgeon upon pulling the medical apparatus again out of the vessel 301. If and when the surgeon feels the tactile feedback, he or she knows that the medical apparatus is ideally placed with respect to the aperture 302 in order to close it by releasing closing devices 600.

FIG. 35 shows parts of yet another embodiment of the medical apparatus from its side. FIG. 35 shows substantially what is also revealed in FIG. 33 or FIG. 33A. However, it also shows in a highly schematic manner two closing devices 600 closing the aperture 302. The engaging devices 410 have still to be folded again and withdrawn from the vessel lumen 1006.

Figure 36:
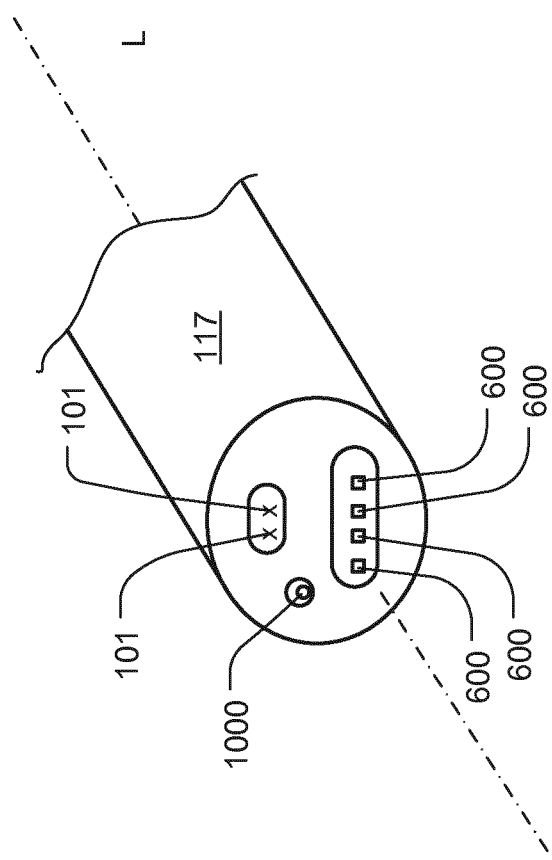
FIG. 36 shows a highly simplified view onto the front-end surface of the medical apparatus.

FIG. 36 shows a highly simplified view onto the front-end surface of the medical apparatus having a longitudinal axis L and a casing 117, in yet another embodiment. As can be seen, the end of the medical apparatus has several openings. One houses the guide wire 1000, one houses two retracting devices 101, one houses four closing devices 600.

It goes without saying that the number of openings, retracting devices 101 and closing devices 600 is not limit to the number shown in FIG. 36. Also, the guide wire 1000 may run through an opening used exclusively for the guide wire 1000. However, it could also share its opening with the retracting device or devices 101 and/or the closing devices 600.

It will be appreciated by those skilled in the art that although the description is made to preferred embodiments, the disclosure and description in many respects, is only illustrative and not restrictive, susceptible to various modifications and alternative forms. Changes may be made in details, particularly in matters of shape, size, material and arrangement of parts without exceeding the scope of the invention. It should be understood, however, that the invention is not to be limited to the particular forms or methods disclosed, but to the contrary, the invention is to cover all modifications, equivalents and alternatives.

Accordingly, the scope of the invention is defined in the claims.

LIST OF REFERENCE NUMERALS 100 retracting unit
101 retracting device
102 retracting device holder
108 arrow
110 distal tip of retracting device holder, end, distal end
111 proximal end
112 distal end
115 guide wire lumen
117 casing
202 suture, holding device
203 piston
204 groove
207 groove
301 vessel, vessel wall, tissue
302 (vessel) aperture, slit opening, aperture opening
410 engaging device
420 curve, step
600 closing device
602 proximal end, junction, groove
603 distal end, pointed end, closing member, tip of the closing device, end of the closing device
604 arm
605 curled or curved section
708 anchor, anchor form of the closing device
709 tip 603 penetrates the tissue wall
722 perforation of 603
800 closing member
801 longitudinal direction arrow, arrow indicating orientation of support/closing device holder
802 closing device holder
803 channel, lateral channel
804 distal end, closing device holder end
805 proximal end, closing device holder end
1000 guide wire
1006 vessel lumen 1411 aperture wall, edge
1420 arrow
1421 upward movement
1422 angle
1722 protractor
2204 wall, aperture wall, long sides
2600 suture
2700 arrow
L longitudinal axis

The invention claimed is:

1. A medical apparatus for closing an aperture in a tissue a of a patient, wherein the aperture comprises an opening, an incision, a puncture, a passage through tissue and/or a communication with a blood vessel or other body lumen, the medical apparatus comprising:
a closing device holder, for releasably receiving one or more closing devices, wherein the closing device holder has a distal end configured for being advanced through or into the aperture, and wherein the distal end of the closing device holder has at least one channel allowing the closing device to exit the closing device holder; and
a retracting unit to come into contact with opposite sides of the aperture for at least one of
(i) retracting the opposite sides of the aperture, and
(ii) spreading the aperture,
causing the aperture to change its shape into a slit or a slit-like or a more slit-like aperture or to spread or to augment the dimension or diameter of the aperture in at least one or in exactly one dimension of the aperture, the retracting unit comprising:
at least one retracting device holder;
at least one retracting device; and
at least one engaging device connected to said retracting device, wherein the engaging device and the retracting device are configured for engaging with the tissue surrounding the aperture from within or from below the aperture.

2. The medical apparatus according to claim 1,
wherein the retracting device is at least partially releasably received in the retracting device holder;
wherein the retracting device is arranged in a moveable or slidable manner with respect to the retracting device holder.

3. The medical apparatus according to claim 1, wherein the retracting device is arranged in a moveable or slidable manner with respect to the retracting device holder.

4. The medical apparatus according to claim 1, wherein the engaging device is configured to be foldable and/or to be comprised or captured at least partially within the retracting device holder.

5. The medical apparatus according to claim 4, wherein the at least one retracting device comprising at least two retracting devices and/or the at least one engaging device comprising at least two engaging devices are captured within the retracting device holder in a releasable manner, in particular such that they are arranged to be at least partly released from the retracting device holder by manipulating the retracting device holder or the engaging device, in particular to be positioned below the opening level of the aperture which is to be closed.

6. The medical apparatus according to claim 1, wherein the retracting device holder and/or the retracting device and/or said engaging device are configured to retract the opposite sides of the aperture, in particular such that the aperture changes its shape, from a rather round aperture, to a slit aperture, such that the extended transverse diameter is at least double the length of the retracted longitudinal diameter of the aperture.

7. The medical apparatus according to claim 1,
wherein the retracting unit is characterized by:
(i) the at least one retracting device having a first side and an opposite second side, or
(ii) the at least one retracting device having a first arm and a second arm, or
(iii) the at least one retracting device comprising a first retracting device and a second retracting device, or
(iv) the at least one retracting device holder comprising a first retracting device holder and a second retracting device holder, or
(v) the at least one engaging device comprising a first engaging device and a second engaging device, or
(vi) a combination thereof;
and
wherein the retracting unit comprises:
a mechanism for moving the first side apart or away from the second side, the first arm apart or away from the second arm, the first retracting device apart or away from the second retracting device, the first retracting device holder apart or away from the second retracting device holder and/or the first engaging device apart or away from the second engaging device.

8. The medical apparatus according to claim 7, wherein the mechanism comprises or consists of a shape memory characteristic.

9. The medical apparatus according to claim 1, comprising:
a closing device comprised in the closing device holder.

10. The medical apparatus according to claim 1, wherein the closing device is at least partially comprised within the closing device holder in a stressed state, in particular within the distal end of the closing device holder, in particular when the medical apparatus is in an undeployed state; wherein the closing device has two or more ends and a junction connecting with the two or more ends, via two or more arms.

11. The medical apparatus according to claim 10, wherein the closing device is comprised within the closing device holder such that when the closing device is manipulated to exit the distal end of the closing device holder during the use of the medical apparatus, the closing device releases its stress or part of its stress by bending the two or more arms outside of the closing device holder, whereby the two or more ends are arranged to perforate the inner wall of the tissue surrounding the aperture.

12. The medical apparatus according to claim 1, wherein at least part of the closing device, the retracting device, the retracting device holder and/or the engaging device is made of a deformable shape memory alloy and/or has a self-expanding shape memory section or wire body.

13. The medical apparatus according to claim 1, wherein at least part of the closing device, the retracting device, the retracting device holder and/or the engaging device is made of Nitinol.

14. The medical apparatus according to claim 1, wherein at least part of the closing device, the retracting device, the retracting device holder and/or the engaging device is made of biocompatible and/or bio-absorbable material.

15. The medical apparatus according to claim 14, wherein the biocompatible and/or bio-absorbable material is at least one material selected from the group consisting of Ti, Ti alloys, Nitinol, stainless steel, polymeric materials, and ceramic.

16. The medical apparatus according to claim 1, wherein the closing device or parts thereof curl into a closed form when in a stress-free state.

17. The medical apparatus according to claim 1, wherein the closing device or parts thereof curl into a loop- or ring- or circle-like shape when in a stress-free state.

18. The medical apparatus according to claim 1, wherein the closing device after deployment, has a cross-sectional dimension ranging from 10 micrometers to 1 centimeter, from 40 micrometers to 200 micrometers, or from 50 micrometers to 100 micrometers.

19. The medical apparatus according to claim 1, further comprising a pushing device, extending through the proximal end of the closing device holder, for the manipulation of the closing device.

20. The medical apparatus according to claim 19, wherein the pushing device is a rod or piston.

21. The medical apparatus according to claim 19,
further comprising a holding device extending through the proximal end of the closing device holder for the manipulation of the closing device, wherein the holding device is attached to the closing device; and
wherein the closing device holder comprises an elongate tube defining a longitudinal direction of the closing device holder, and wherein the closing device holder has one or more grooves on an inner wall of the tube and and/or one or more grooves on the pushing device for guiding the holding device along the longitudinal direction of the closing device holder, wherein the one or more grooves is defined in a section of the inner wall of the tube or the pushing device that is transverse to the longitudinal direction.

22. The medical apparatus according to claim 1, further comprising a holding device extending through the proximal end of the closing device holder for the manipulation of the closing device, wherein said holding device is attached to the closing device.

23. The medical apparatus according to claim 22,
wherein the holding device is a string or suture.

24. The medical apparatus according to claim 1, wherein the at least one channel comprises two or more channels on a wall of the closing device holder, allowing the one or more ends of the closing device to exit the closing device holder upon manipulation of the medical apparatus or when required by a user.

25. The medical apparatus according to claim 1, wherein the at least one channel comprises two channels arranged opposite to each other on a wall of the closing device holder.

26. The medical apparatus according to claim 1, wherein the retracting device holder comprises an elongated tube, comprising or consisting of metal or plastic, configured to capture the retracting device.

27. A method for closing an aperture of a tissue, encompassing the steps:
providing a medical apparatus according to claim 1; and
closing the aperture by means of the medical apparatus.

28. The method according to claim 27, further comprising the steps:
introducing parts of the retracting unit into the aperture;
contacting opposite sides of the aperture with the retracting unit or elements comprised by it;
retracting the opposite sides of the aperture and/or spreading the aperture with the retracting unit or elements comprised by it; and
releasing at least one closing device from the closing device holder and connecting the opposite sides of the aperture to each other with the closing device.

29. The method according to claim 28, wherein the step of retracting opposite sides of the aperture and/or spreading the aperture causes the aperture to change its shape into a slit or a slit-like or a more slit-like aperture or to spread or to augment the dimension or diameter of the aperture in at least one or in exactly one dimension of the aperture.

* * * * *